(12) United States Patent
Tajima

(10) Patent No.: US 8,923,482 B2
(45) Date of Patent: Dec. 30, 2014

(54) RADIATION IMAGE DETECTING DEVICE AND CONTROL METHOD THEREOF, AND RADIATION IMAGING SYSTEM

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 163 days.

(21) Appl. No.: 13/793,742

(22) Filed: Mar. 11, 2013

(65) Prior Publication Data

US 2013/0251106 A1  Sep. 26, 2013

(30) Foreign Application Priority Data

Mar. 23, 2012 (JP) ................. 2012-067176

(51) Int. Cl.
*A61B 6/00* (2006.01)
*H05G 1/44* (2006.01)

(52) U.S. Cl.
CPC ........ *H05G 1/44* (2013.01); *A61B 6/542* (2013.01); *A61B 6/548* (2013.01)
USPC ............................................ 378/97; 378/108

(58) Field of Classification Search
CPC ............................. A61B 6/542; A61B 6/4233
USPC ......................... 378/197, 108, 114
See application file for complete search history.

(56) References Cited

U.S. PATENT DOCUMENTS

| 2004/0101100 A1* | 5/2004 | Morii et al. ................. 378/98.7 |
| 2008/0240346 A1* | 10/2008 | Kashiwagi et al. ............. 378/37 |
| 2011/0249799 A1* | 10/2011 | Lalena et al. .................. 378/97 |

FOREIGN PATENT DOCUMENTS

| JP | 5-110949 A | 4/1993 |
| JP | 2002-590 A | 1/2002 |
| JP | 2008-117641 A | 5/2008 |
| JP | 2011-10870 A | 1/2011 |

* cited by examiner

*Primary Examiner* — Hoon Song
(74) *Attorney, Agent, or Firm* — Birch, Stewart, Kolasch & Birch, LLP

(57) ABSTRACT

An AEC section of an electronic cassette includes a measurement area setting circuit for setting a measurement area in an imaging surface. The measurement area setting circuit is switchable between a specified area mode and an automatic area setting mode. In the specified area mode, a first measurement area is set up in a position predetermined in accordance with a body part to be imaged. In the automatic area setting mode, a second measurement area is set up based on the distribution of an X-ray dose measured by measuring pixels. X-ray emission time is shortened in the specified area mode, because the setting of the first measurement area is quickly performed. The automatic area setting mode eliminates the need for troublesome positioning between a patient and an FPD.

14 Claims, 25 Drawing Sheets

FIG. 7

| BODY PART TO BE IMAGED | TUBE VOLTAGE (kV) | FIRST MEASUREMENT AREA | EMISSION STOP THRESHOLD VALUE |
|---|---|---|---|
| ... | ... | ... | ... |
| CHEST AP | V1 | (X, Y) COORDINATES = ($\alpha$, $\beta$) | TH1 |
| CHEST PA | V2 | (X, Y) COORDINATES = ($\alpha$, $\beta$) | TH2 |
| ... | ... | ... | ... |

FIG. 12

| BODY PART TO BE IMAGED | MODE TO BE SELECTED |
|---|---|
| ⋮ | ⋮ |
| CHEST AP | SPECIFIED AREA MODE |
| CHEST PA | SPECIFIED AREA MODE |
| HEAD PA | AUTOMATIC AREA SETTING MODE |
| CHEST OBLIQUE | AUTOMATIC AREA SETTING MODE |
| ⋮ | ⋮ |

RADIATION IMAGE DETECTING DEVICE AND CONTROL METHOD THEREOF, AND RADIATION IMAGING SYSTEM

BACKGROUND OF THE INVENTION

1. Field of the Invention

The present invention relates to a radiation image detecting device that performs automatic exposure control and a control method thereof, and a radiation imaging system.

2. Description Related to the Prior Art

In a medical field, a radiation imaging system, for example, an X-ray imaging system using X-rays is widely known. The X-ray imaging system is constituted of an X-ray generating device having an X-ray source for emitting X-rays and an X-ray image detecting device for detecting an X-ray image. A type of X-ray image detecting device using a flat panel detector (FPD), which has a matrix of pixels each for accumulating electric charge in accordance with the amount of the X-rays incident thereon, as a detection panel becomes widespread. The FPD accumulates the electric charge on a pixel-by-pixel basis, and converts the accumulated electric charge into a voltage signal in its signal processing circuit to output the X-ray image of an object as digital image data.

In X-ray imaging, it is required to apply just the right amount of radiation dose to the object (patient) without excess and deficiency. Thus, the X-ray imaging system performs automatic exposure control (AEC) by which a radiation dose is measured using the FPD, and X-ray emission is automatically stopped when the radiation dose has reached a predetermined value. In the AEC, a region of space used for measuring the radiation dose is called a measurement field. The pixels of the FPD included in the measurement field are used for measuring the radiation dose. Therefore, the choice of the measurement field translates into the choice of the pixels to be used for measuring the radiation dose, in other words, the setting of a measurement area in the FPD. Generally speaking, with the aim of having optimal image density at a region of interest (ROI) being the most notable in diagnosis, a region of radiation passed through the ROI is chosen as the measurement field. The measurement field is determined in accordance with a body part to be imaged. Taking chest imaging as an example, a region of radiation passed through the lungs is designated as the measurement field.

Japanese Patent Laid-Open Publication No. 2002-000590 discloses an X-ray image detecting device in which when the body part such as chest or abdomen is designated in a body part setter, a pixel selector chooses the pixels of the FPD and the measurement field is automatically set. Japanese Patent Laid-Open Publication No. 2011-010870 discloses an X-ray imaging device in which an imaging surface of the FPD is partitioned into a plurality of areas (measurement areas). In the X-ray imaging device, a current integrating means integrates electric current flowing through the pixels of each area, and a measurement field determining means automatically determines the measurement field by comparing the integrated values. To be more specific, the area having the lowest integrated value is determined as the measurement field, because if an area receiving the least radiation dose has predetermined image density, the other areas necessarily have image quality higher than predetermined quality.

According to the Japanese Patent Laid-Open Publication No. 2002-000590, the measurement field is determined in accordance with the designated body part. In order to appropriately perform the AEC, it is required that the measurement field and the ROI of the patient are accurately positioned so as to coincide with each other.

Especially in oblique imaging in which the X-rays are applied to the patient in an oblique direction, since the measurement field is skewed with respect to the FPD, it is difficult to achieve precise positioning among the X-ray source, the FPD, and the ROI. Inappropriate positioning allows the X-rays that have not passed through the ROI to enter the measurement field. This causes excess or deficiency of an X-ray dose, and deteriorates the image quality of the ROI.

The Japanese Patent Laid-Open Publication No. 2011-010870 does not bring about the above problem, because the measurement field is automatically set up based on the distribution of the actually measured X-ray dose. However, the image quality of the ROI could vary depending on the position of the measurement field automatically set up in imaging. Also, an automatic setting process of the measurement field requires much time, as compared with a manual setting process by which the position of the measurement field is determined in accordance with the body part, and hence elongates X-ray emission time. The longer the X-ray emission time, the more the X-ray exposure of the patient increases and the likelier a blur occurs in the X-ray image by the effect of a body motion of the patient.

SUMMARY OF THE INVENTION

An object of the present invention is to provide a radiation image detecting device that has a specified area mode for setting a measurement field in a position predetermined in accordance with a body part to be imaged and an automatic area setting mode for setting the measurement field based on the distribution of an X-ray dose, a control method thereof, and a radiation imaging system.

To achieve the above and other objects, a radiation image detecting device according to the present invention includes a detection panel, a plurality of dose measuring sensors, and an AEC section. The detection panel has an imaging surface having a plurality of pixels arranged in two dimensions, and detects a radiation image of an object from electric charge accumulated in the pixels in accordance with radiation emitted from a radiation source and passed through the object. The plurality of dose measuring sensors are disposed in the imaging surface. The AEC section performs automatic exposure control based on signals from the dose measuring sensors. The AEC section includes a measurement area setting circuit, a mode switching circuit, an integration circuit, and a comparison circuit. The measurement area setting circuit sets up a measurement area to be used for measuring a radiation dose on the imaging surface. The measurement area setting circuit is switchable between a specified area mode for performing an area selecting process to set up a first measurement area in a position predetermined in accordance with a body part to be imaged and an automatic area setting mode for performing an automatic area setting process to set up a second measurement area based on the distribution of the radiation dose measured by the dose measuring sensors. The mode switching circuit switches the measurement area setting circuit between the specified area mode and the automatic area setting mode. The integration circuit integrates the signal from the dose measuring sensor present within the first or second measurement area, in order to obtain an integrated value corresponding to the radiation dose. The comparison circuit compares the integrated value with a predetermined emission stop threshold value. When the integrated value has reached the emission stop threshold value, the comparison circuit outputs an emission stop signal to stop radiation emission from the radiation source.

The mode switching circuit preferably chooses one of the specified area mode and the automatic area setting mode in response to an operation from outside, or in accordance with the body part of the object.

The mode switching circuit preferably includes an emission time predicting unit for predicting emission time of the radiation based on an imaging condition and an emission time comparing unit for comparing the predicted emission time with a predetermined mode switching threshold value. The mode switching circuit chooses the specified area mode, when the predicted emission time is less than the mode switching threshold value. The mode switching circuit chooses the automatic area setting mode, when the predicted emission time is more than the mode switching threshold value.

The measurement area setting circuit preferably has a combination mode for using the specified area mode and the automatic area setting mode in conjunction with each other. The mode switching circuit switches the measurement area setting circuit among the specified area mode, the automatic area setting mode, and the combination mode.

When the measurement area setting circuit is put into the combination mode, the AEC section preferably performs the steps of setting up the first measurement area by the area selecting process; starting setting up the second measurement area by the automatic area setting process, in parallel with the area selecting process; integrating the signal from the dose measuring sensor present within the first measurement area with use of the integration circuit, to calculate a first integrated value corresponding to the radiation dose; comparing the first integrated value with the emission stop threshold value; when the first integrated value has reached the emission stop threshold value, outputting the emission stop signal in order to stop the radiation emission from the radiation source; when setup of the second measurement area is completed before the first integrated value has reached the emission stop threshold value, the integration circuit stopping calculating the first integrated value, and integrating the signal from the dose measuring sensor present within the second measurement area to calculate a second integrated value; and when the second integrated value has reached the emission stop threshold value, outputting the emission stop signal in order to stop the radiation emission from the radiation source.

When the measurement area setting circuit is put into the combination mode, the AEC section preferably performs the steps of setting up a temporary measurement area by the area selecting process; setting up an actual measurement area in the temporary measurement area by performing the automatic area setting process in the temporary measurement area; and performing the automatic exposure control by using the radiation dose measured by the dose measuring sensor present within the actual measurement area. The temporary measurement area is preferably larger in size than the first measurement area.

When the measurement area setting circuit is put into the combination mode, the AEC section preferably performs the steps of setting up the first measurement area by the area selecting process; performing the automatic area setting process in parallel with the area selecting process; and adjusting a position of the first measurement area based on distribution of the radiation dose obtained by the automatic area setting process.

The AEC section preferably further includes an imaging error detection circuit for detecting an imaging error based on the radiation dose measured by the dose measuring sensor present within the first measurement area. When the imaging error detection circuit detects the imaging error, the mode switching circuit preferably chooses the automatic area setting mode. When the imaging error detection circuit detects no imaging error, the mode switching circuit preferably chooses the specified area mode.

The plurality of pixels may include a plurality of normal pixels and a plurality of measuring pixels used as the dose measuring sensors. Each normal pixel performs accumulation of the electric charge and readout of the electric charge to a signal line in accordance with operation of a switching element. Each measuring pixel is connected to the signal line directly without through the switching element, or connected to another switching element that is different from the switching element of the normal pixels.

A control method of a radiation image detecting device includes the steps of switching the AEC section between a specified area mode and an automatic area setting mode, an area selecting process being performed in the specified area mode to set up a first measurement area in a position predetermined in accordance with a body part to be imaged of an object, an automatic area setting process being performed in the automatic area setting mode to set up a second measurement area based on the distribution of a radiation dose measured by dose measuring sensors; performing a chosen one of the area selecting process and the automatic area setting process in order to set up one of the first and second measurement areas; integrating a signal from the dose measuring sensor present within one of the first and second measurement areas to obtain an integrated value corresponding to the radiation dose; comparing the integrated value with a predetermined emission stop threshold value; and when the integrated value has reached the emission stop threshold value, outputting an emission stop signal to stop radiation emission from a radiation source.

A radiation imaging system includes a radiation source for emitting radiation and the radiation image detecting device described above.

According to the present invention, the measurement area setting circuit has the specified area mode and the automatic measurement area setting mode, and is arbitrary switchable therebetween. Thus, it is possible to use the optimal mode in accordance with an imaging situation including a patient's condition and the body part. The specified area mode eliminates the demerits of the automatic area setting mode, and contrarily, the automatic area setting mode eliminates the demerits of the specified area mode.

In the automatic area setting mode, a measurement field coincides with a ROI without performing troublesome positioning between the body part of the patient and the measurement field. Especially even in oblique imaging in which the positional relation among the X-ray source, the body part, and the measurement field is hard to grasp, the measurement field is set up in an appropriate position without performing the troublesome positioning, so the AEC is appropriately carried out.

In the specified area mode, the measurement area is set up in a position predetermined in accordance with the body part to be imaged. Thus, the specified area mode needs less time for setting up the measurement area. Therefore, the X-ray emission time is more shortened in the specified area mode than in the automatic area setting mode. This reduces unnecessary radiation exposure of the patient, and prevents the occurrence of a blur in the radiation image due to a body motion. Also, since the measurement field is fixed in accordance with the body part, if there is any problem in the image quality of the radiation image, the problem could be solved easily only by checking the positioning between the measurement field and the body part to be imaged.

Also, the provision of the combination mode, which uses the specified area mode and the automatic area setting mode in conjunction with each other, facilitates optimal AEC performance in accordance with the actual imaging situation.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 7 is a table of imaging conditions stored in a console;
FIG. 12 is an explanatory view of combinations of a body part and a chosen mode in the second embodiment.

DESCRIPTION OF THE PREFERRED EMBODIMENTS

First Embodiment

Figure 1:
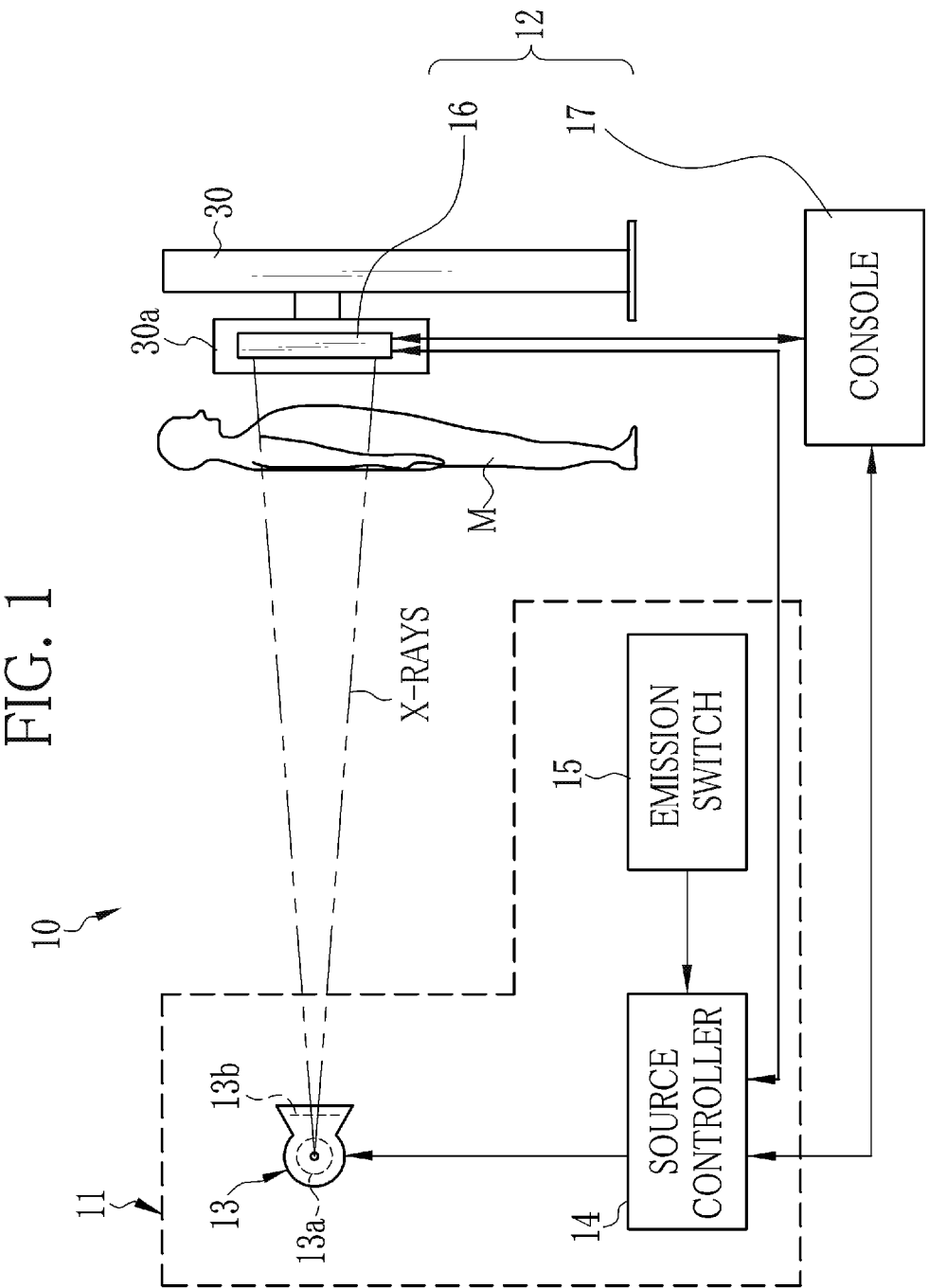
FIG. 1 is a schematic view of an X-ray imaging system.

As shown in FIG. 1, an X-ray imaging system 10 is constituted of an X-ray generating device 11 for generating X-rays and an X-ray image detecting device 12 for producing an X-ray image from the X-rays passed through a body part being an object of a patient M. The X-ray generating device 11 includes an X-ray source 13 for emitting the X-rays, a source controller 14 for controlling the X-ray source 13, and an emission switch 15 for commanding the start of X-ray emission. The X-ray image detecting device 12 includes an electronic cassette 16 for detecting an X-ray image and a console 17 for controlling the electronic cassette 16. The source controller 14, the electronic cassette 16, and the console 17 are communicatably connected to each other through a wired or wireless communication unit.

The X-ray source 13 has an X-ray tube 13a for emitting the X-rays and a collimator 13b for limiting an irradiation field of the X-rays. The X-ray tube 13a has a cathode being a filament for emitting thermoelectrons and an anode (target) that radiates the X-rays by collision of the thermoelectrons emitted from the cathode. The collimator 13b is composed of, for example, four X-ray shielding lead plates disposed on each side of a rectangle so as to form an irradiation opening in its middle through which the X-rays propagate. A shift of the lead plates varies the size of the irradiation opening to limit the irradiation field.

Figure 2:
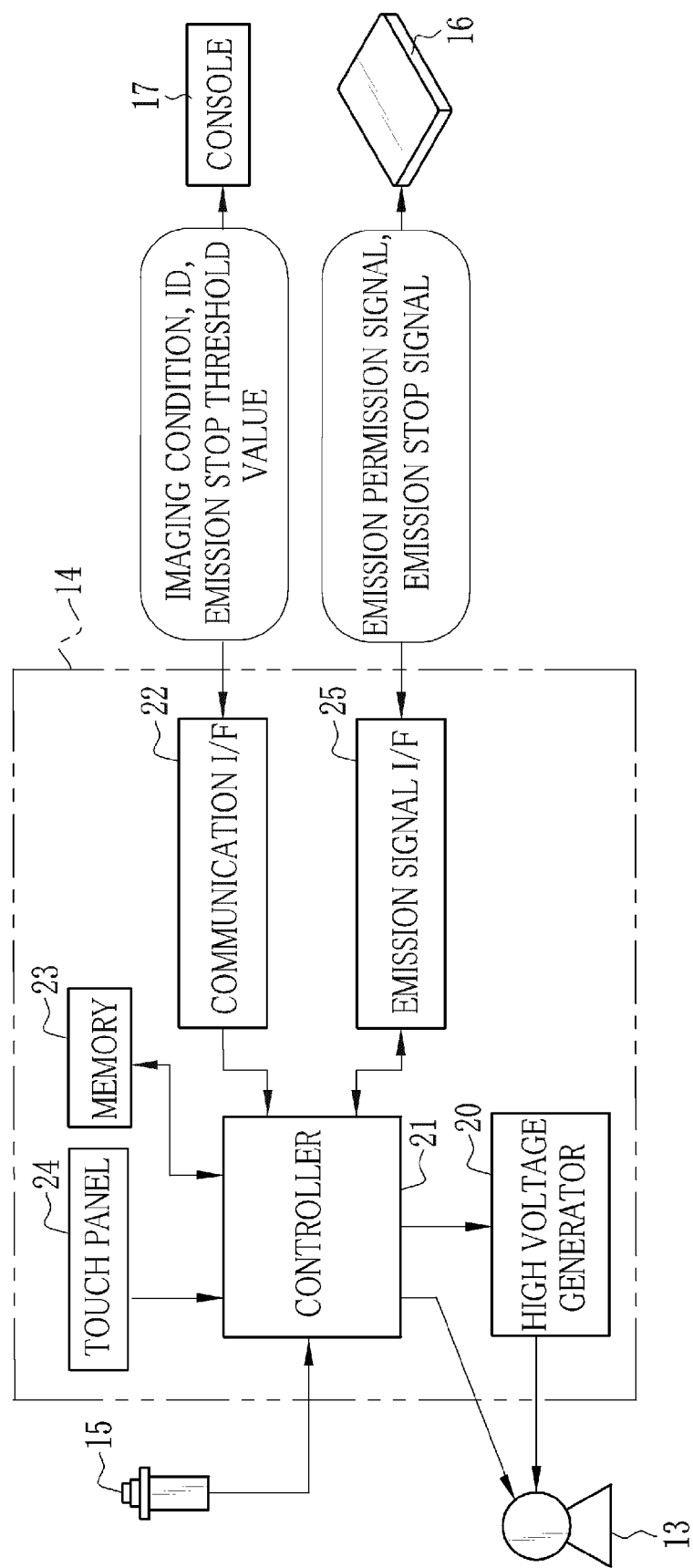
FIG. 2 is a block diagram of a source controller.

As shown in FIG. 2, the source controller 14 includes a high voltage generator 20, a controller 21, and a communication I/F 22. The high voltage generator 20 generates high tube voltage by multiplying input voltage by a transformer, and supplies the tube voltage to the X-ray source 13 through a high voltage cable. The controller 21 controls the tube voltage for determining an energy spectrum of the X-rays emitted from the X-ray source 13, tube current for determining an emission amount per unit of time, and X-ray emission time. The communication I/F 22 mediates transmission of information and signals from and to the console 17.

The emission switch 15, a memory 23, and a touch panel 24 are connected to the controller 21. The emission switch 15 is a switch operated by a radiological technician at the start of imaging, and is a two-step press switch, for example. Upon a half press of the emission switch 15, a warm-up start signal is issued to start warming up the X-ray source 13. Upon a full press, an emission start signal is issued to start the X-ray emission from the X-ray source 13. The warm-up start signal and the emission start signal are inputted to the source controller 14 through a signal cable. Upon receiving the emission start signal from the emission switch 15, the controller 21 starts electric power supply from the high voltage generator 20 to the X-ray source 13.

Several types of imaging conditions each including the tube voltage and a tube current-time product (mAs) are stored in advance in the memory 23. The radiological technician manually chooses an appropriate imaging condition from the several types of imaging conditions through the touch panel 24. The source controller 14 applies the X-rays based on the tube voltage and the tube current-time product (the product of the tube voltage and maximum emission time) of the chosen imaging condition. In AEC, an X-ray dose applied to an FPD 35 is measured. When it is detected that the applied X-ray dose has reached a required value, the X-ray emission is stopped even if actual emission time has not yet reached the maximum emission time. Note that, the maximum emission time is set at time that allows obtainment of the X-ray image usable in diagnosis without an excess of the X-ray dose, even if the X-ray emission is not stopped by the AEC. The imaging condition may be transmitted from the console 17 through the communication I/F 22.

An emission signal I/F 25 is connected to the electronic cassette 16 to regulate the stop timing of the X-ray emission based on outputs of measuring pixels 65 (see FIG. 3) of the electronic cassette 16. In this case, upon receiving the warm-up start signal from the emission switch 15, the controller 21 transmits a query signal to the electronic cassette 16 thorough the emission signal I/F 25. In response to the query signal, the electronic cassette 16 performs a preparation process, which includes the completion of reset operation and the start of charge accumulation operation. After that, when the controller 21 receives an emission permission signal, being a response of the query signal, from the electronic cassette 16 at the emission signal I/F 25 and further receives the emission start signal from the emission switch 15, the controller 21 starts electric power supply from the high voltage generator 20 to the X-ray source 13. The electronic cassette 16 measures the received X-rays. When it is detected that the received X-ray dose has reached a predetermined value, the electronic cassette 16 issues an emission stop signal. Upon receiving the emission stop signal by the emission signal I/F 25, the controller 21 stops the electric power supply from the high voltage generator 20 to the X-ray source 13 to stop the X-ray emission. The controller 21 has a timer used for stopping the X-ray emission when the set emission time has elapsed, in addition to the function of stopping the X-ray emission in response to the emission stop signal.

As is widely known, the electronic cassette 16 is composed of the FPD 35 and a portable housing (not shown) containing the FPD 35. The housing of the electronic cassette 16 is in the shape of an approximately rectangular flat box. The size of the housing is compatible with the international standard ISO 4090:2001, just as with a film cassette and an IP cassette (also called CR cassette). Thus, the electronic cassette 16 is loadable in an existing imaging stand designed for the film cassette and the IP cassette.

As shown in FIG. 1, the electronic cassette 16 is detachably set on a holder 30a of an imaging stand 30 in such a position that an imaging surface 36 of the FPD 35 is opposed to the X-ray source 13. In addition, the electronic cassette 16 is usable by itself in a state of being put on a bed under the patient M lying, or being held by the patient M himself/herself.

Figure 3:
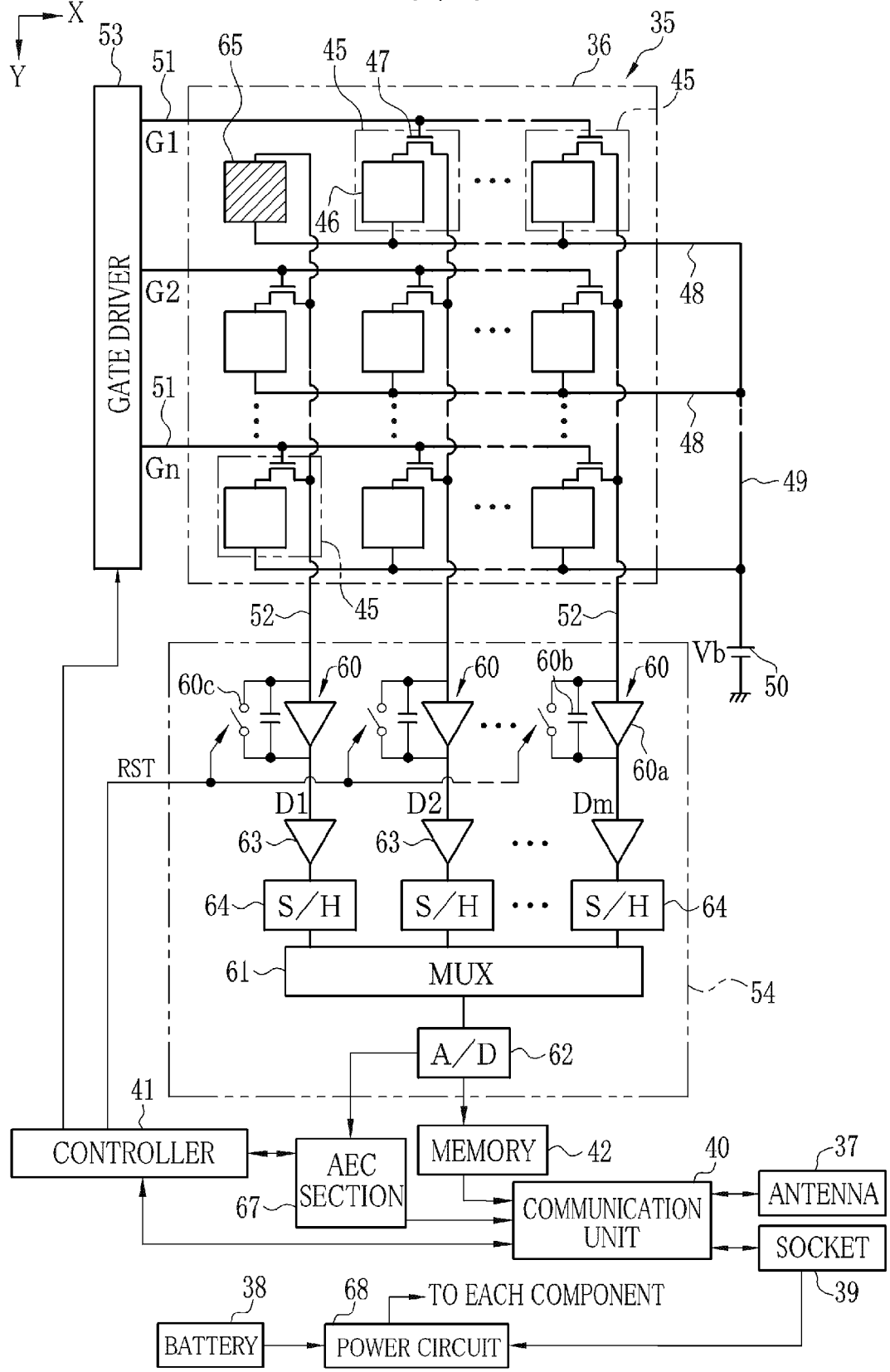
FIG. 3 is a block diagram of an electronic cassette.

As shown in FIG. 3, the electronic cassette 16 contains an antenna 37 and a battery 38 to enable wireless communication with the console 17. The antenna 37 transmits and receives a radio wave for the wireless communication to and from the console 17. The battery 38 supplies electric power to each component of the electronic cassette 16 through a power circuit 68. The battery 38 is small enough to be contained in the slim electronic cassette 16. The battery 38 can be taken out of the electronic cassette 16 and mounted on a specific cradle for recharging. Alternatively, the battery 38 may be recharged by a wireless power feeder.

In addition to the antenna 37, the electronic cassette 16 is provided with a socket 39. The socket 39 is used for establishing wired communication with the console 17, in such a case where the wireless communication between the electronic cassette 16 and the console 17 is disabled due to a shortage of the battery 38 or the like. Connecting a cable of the console 17 to the socket 39 enables the wired communication with the console 17. At this time, the console 17 feeds the electric power to the electronic cassette 16 through the power circuit 68.

The antenna 37 and the socket 39 are connected to a communication unit 40. The communication unit 40 mediates the transmission and reception of various types of information and signals including image data among the antenna 37 or the socket 39, a controller 41, and a memory 42.

The FPD 35 has the imaging surface 36 that has a TFT active matrix substrate and a plurality of pixels 45 and 65, which are arranged on the TFT active matrix substrate in two dimensions. Each of the pixels 45 and 65 produces electric charge in accordance with the amount of X-rays incident thereon. The plurality of pixels 45 and 65 are arranged into a matrix of n rows (X direction) and m columns (Y direction) at a predetermined pitch.

The FPD 35 is of an indirect conversion type, having a scintillator (phosphor) for converting the X-rays into visible light. The pixels 45 perform photoelectric conversion of the visible light produced by the scintillator. The scintillator is made of CsI (cesium iodide), GOS (gadolinium oxysulfide), or the like, and is opposed to the entire imaging surface 36 having the matrix of pixels 45. The scintillator and the TFT active matrix substrate may adopt either a PSS (penetration side sampling) method or an ISS (irradiation side sampling) method. In the PSS method, the scintillator and the substrate are disposed in this order from an X-ray incident side. In the ISS method, the scintillator and the substrate are disposed in reverse order. Note that, a direct conversion type FPD, which has a conversion layer (amorphous selenium or the like) for directly converting the X-rays into the electric charge, may be used instead.

The pixel (normal pixel) 45 is composed of a photodiode 46, a capacitor (not shown), and a thin film transistor (TFT) 47. The photodiode 46 being a photoelectric conversion element produces the electric charge (electron and hole pairs) upon entry of the visible light. The capacitor accumulates the electric charge produced by the photodiode 46. The TFT 47 functions as a switching element.

The photodiode 46 is composed of a semiconducting layer (of a PIN type, for example) for producing the electric charge, and upper and lower electrodes disposed on the top and bottom of the semiconducting layer. The lower electrode of the photodiode 46 is connected to the TFT 47. The upper electrode of the photodiode 46 is connected to a bias line 48. The number of the bias lines 48 coincides with the number of rows (n rows) of the pixels 45 arranged in the imaging surface 36. All the n bias lines 48 are connected to a bias power source 50 through a bus 49. The bias power source 50 applies bias voltage Vb to the upper electrode of every photodiode 46 through the bus 49 and the bias lines 48. Since the application of the bias voltage Vb produces an electric field in the semiconducting layer, the electric charge (electron and hole pairs) produced in the semiconducting layer by the photoelectric conversion is attracted to the upper and lower electrodes, one of which has positive polarity and the other has negative polarity. Thereby, the electric charge is accumulated in the capacitor.

A gate electrode of the TFT 47 is connected to a scan line 51. A source electrode of the TFT 47 is connected to a signal line 52. A drain electrode of the TFT 47 is connected to the photodiode 46. The scan lines 51 and the signal lines 52 are routed into a lattice. The number of the scan lines 51 coincides with the number of the rows (n rows) of the pixels 45 arranged in the imaging surface 36. The number of the signal lines 52 coincides with the number of the columns (m columns) of the pixels 45. Every scan line 51 is connected to a gate driver 53, and every signal line 52 is connected to a signal processing circuit 54.

The gate driver 53 drives the TFTs 47 to carry out the charge accumulation operation in which each pixel 45 accumulates the signal charge in accordance with the amount of the X-rays incident thereon, readout operation in which the signal charge is read out from the pixels 45, and the reset operation. The control circuit 41 controls the start timing of the above operation carried out by the gate driver 53.

In the charge accumulation operation, while the TFTs 47 are turned off, the pixels 45 accumulate the signal charge. In the readout operation, the gate driver 53 sequentially issues gate pulses G1 to Gn each of which drives the TFTs 47 of the same row at a time. Thereby, the scan lines 51 are activated one by one so as to turn on the TFTs 47 connected to the activated scan line 51 on a row-by-row basis. Upon turning on the TFT 47, the signal charge accumulated in the capacitor of the pixel 45 is read out to the signal line 52, and inputted to the signal processing circuit 54.

The signal processing circuit 54 includes integration amplifiers 60, a multiplexer (MUX) 61, an A/D converter (A/D) 62, and the like. The integration amplifier 60 is connected to each signal line 52 on a one-by-one basis. The integration amplifier 60 is composed of an operational amplifier 60a and a capacitor 60b connected between input and output terminals of the operational amplifier 60a. One of the input terminals of the operation amplifier 60a is connected to the signal line 52. The other input terminal of the operational amplifier 60a is connected to a ground (GND). A reset switch 60c is connected in parallel with the capacitor 60b. The integration amplifier 60 converts the electric charge inputted from the signal line 52 into each of voltage signals D1 to Dm by integration, and outputs each of the voltage signals D1 to Dm. The output terminal of every operational amplifier 60a is connected to the MUX 61 through another amplifier 63 and a sample holder (S/H) 64. An output of the MUX 61 is connected to the A/D 62.

The MUX 61 sequentially selects one of the plurality of integration amplifiers 60 connected in parallel, and inputs the voltage signals D1 to Dm outputted from the selected integration amplifiers 60 in series to the A/D 62. The A/D 62 converts the inputted voltage signals D1 to Dm into digital data, and outputs the digital data to the memory 42 contained in the electronic cassette 16. Another amplifier may be provided between the MUX 61 and the A/D 62.

After the MUX 61 sequentially reads out from the integration amplifiers 60 the voltage signals D1 to Dm of one row, the controller 41 outputs a reset pulse RST to the integration amplifiers 60 to turn on the reset switches 60c. Thus, the signal charge of one row accumulated in the capacitors 60b is discharged and reset. Upon the reset of the integration amplifiers 60, the gate driver 53 outputs the gate pulse of the next row to start reading out the signal charge from the pixels 45 of the next row. By sequential repetition of this operation, the signal charge is read out from the pixels 45 of every row.

After completion of the readout from every row, the image data representing the X-ray image of one frame is stored in the memory 42. This image data is read out from the memory 42, and outputted to the console 17 through the communication unit 40. Thereby, the electronic cassette 16 detects the X-ray image of the body part.

Dark charge occurs in the semiconducting layer of the photodiode 46 irrespective of the presence or absence of entry of the X-rays. Due to the application of the bias voltage Vb, the dark charge is accumulated in the capacitor of the pixel 45. The dark charge occurring in the normal pixels 45 becomes noise of the image data, and therefore the reset operation is carried out to remove the dark charge. In other words, the reset operation is an operation in which the dark charge produced in the pixels 45 is discharged through the signal lines 52.

The reset operation adopts a sequential reset method, for example, by which the pixels 45 are reset on a row-by-row basis. In the sequential reset method, as with the readout operation of the signal charge, the gate driver 53 sequentially issues the gate pulses G1 to Gn to the signal lines 51 to turn on the TFTs 47 of the pixels 45 on a row-by-row basis. While the TFT 47 is turned on, the dark charge flows from the pixel 45 through the signal line 52 into the capacitor 60b of the integration amplifier 60. In the reset operation, in contrast to the readout operation, the MUX 61 does not read out the electric charge accumulated in the capacitors 60b. In synchronization with the issue of each of the gate pulses G1 to Gn, the controller 41 outputs the reset pulse RST. The reset pulse RST turns on the reset switches 60c, so the electric charge accumulated in the capacitors 60b is discharged, and the integration amplifiers 60 are reset.

Instead of the sequential reset method, a parallel reset method or all pixels reset method may be used. In the parallel reset method, a plurality of rows of pixels are grouped together, and sequential reset is carried out in each group, so as to concurrently discharge the dark charge from the rows of the number of the groups. In the all pixels reset method, the gate pulse is inputted to every row to discharge the dark charge from every pixel at a time. Adoption of the parallel reset method and the all pixel reset method allows speeding up the reset operation.

Upon receiving the inquiry signal from the controller 21 of the source controller 14, the controller 41 performs the reset operation of the FPD 35, and sends the emission permission signal back to the source controller 14. After that, upon receiving the emission start signal, the controller 41 shifts the FPD 35 from the reset operation to the charge accumulation operation.

The FPD 35 has, in the single imaging surface 36, not only the normal pixels 45 each connected to the signal line 52 through the TFT 47, but also a plurality of measuring pixels 65 each of which is connected to the signal line 52 without through the TFT 47. The measuring pixel 65 functions as a dose measuring sensor that measures the X-ray dose applied to the imaging surface 36 through the body part. The number of the measuring pixels 65 is about a few percent of a total pixel number of the imaging surface 36.

Figure 4:
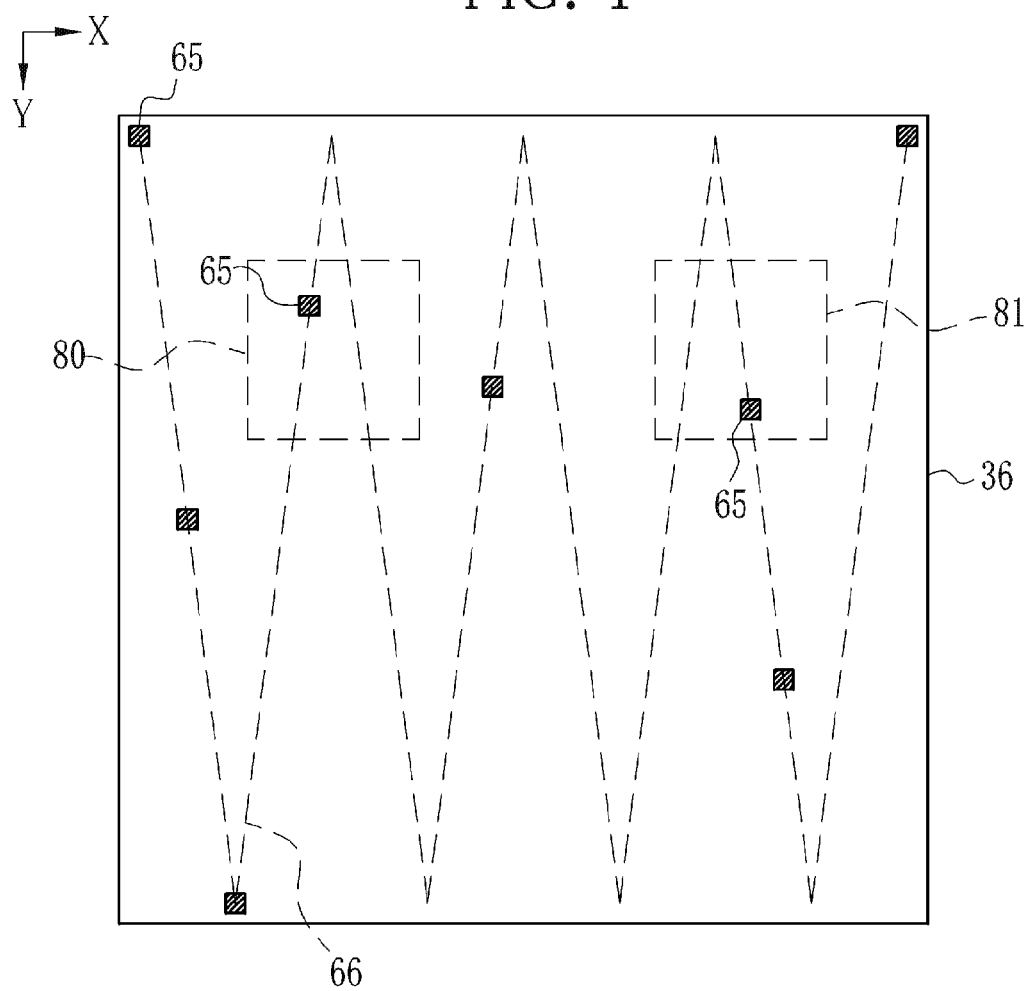
FIG. 4 is an explanatory view of the layout of measuring pixels and first measurement fields in an FPD of the electronic cassette.

As shown in FIG. 4, the measuring pixels 65 are disposed along a zigzag line 66 symmetric with respect to the center of the imaging surface 36 as shown by a broken line, so as to be uniformly distributed in the imaging surface 36 without being localized. For example, one measuring pixel 65 is laid out every two to three signal lines 52, and two or more measuring pixels 65 are not laid out in the single signal line 52. The positions of the measuring pixels 65 are known in manufacturing the FPD 35, and the FPD 35 has a nonvolatile memory (not shown) that stores the position (coordinates) of every measuring pixel 65 in advance. Note that, the disposition of the measuring pixels 65 shown in FIG. 4 is just an example, and is appropriately changeable.

Since the measuring pixel 65 is connected to the signal line 52 directly without through the TFT 47, the signal charge produced in the measuring pixel 65 immediately flows into the signal line 52. The measuring pixel 65 continues outputting the signal charge, even if the normal pixels 45 arranged in the same row as the measuring pixel 65 are in the middle of the charge accumulation operation. Thus, the electric charge produced in the measuring pixel 65 always flows into the capacitor 60b of the integration amplifier 60 in the signal line 52 connected to the measuring pixel 65. This capacitor 60b is charged with voltage in accordance with the X-ray dose incident on the measuring pixel 65. The voltage is taken out at predetermined sampling intervals, and inputted to the A/D 62 through the MUX 61.

The operation of an AEC section 67 is controlled by the controller 41. The AEC section 67 obtains through the A/D 62 the voltage (hereinafter called AEC measurement signals) from the signal lines 52 connected to the measuring pixels 65.

Figure 5:
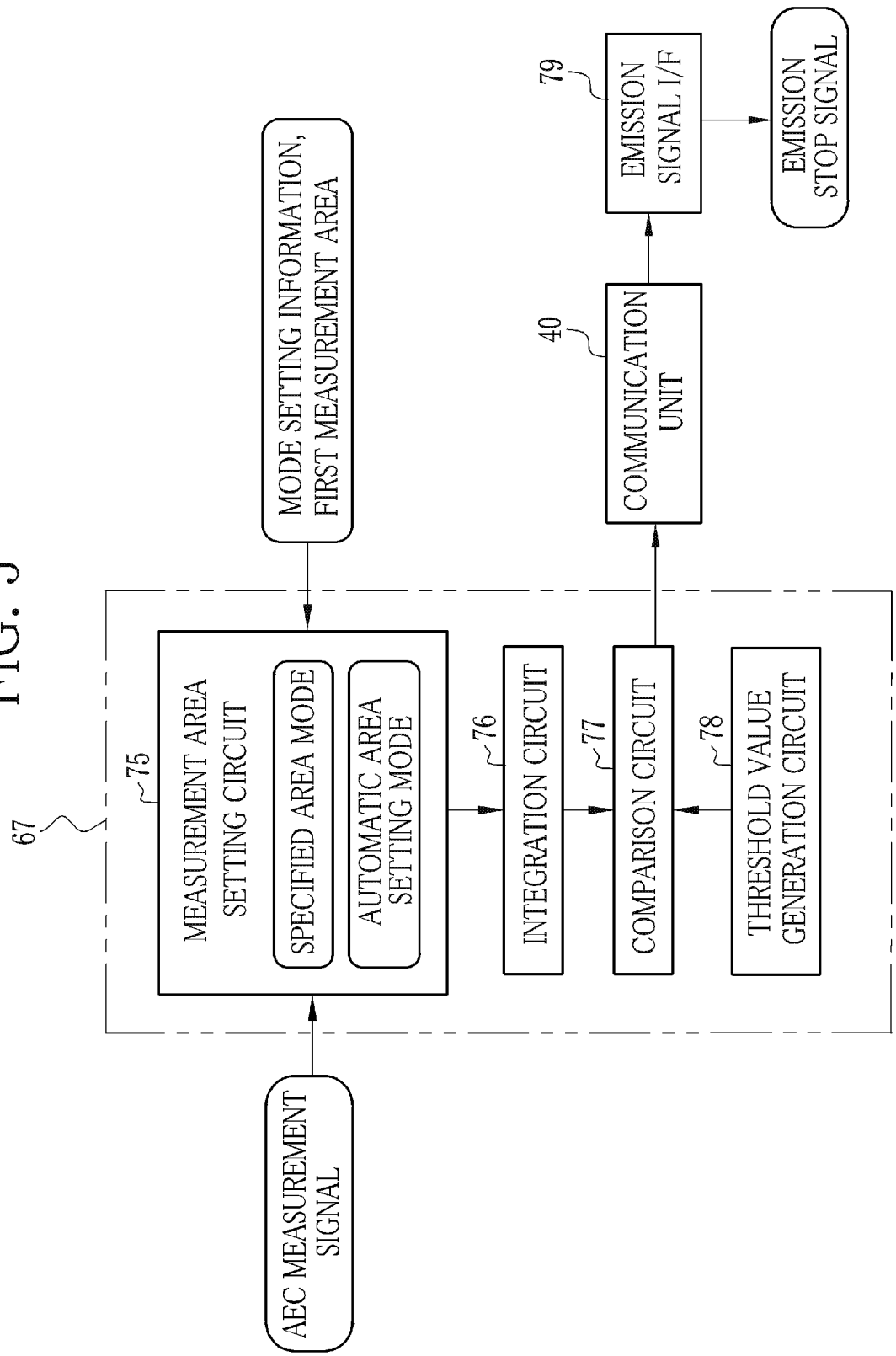
FIG. 5 is a block diagram of an AEC section of the electronic cassette.

As shown in FIG. 5, the AEC section 67 has a measurement area setting circuit 75, an integration circuit 76, a comparison circuit 77, and a threshold value generation circuit 78. The measurement area setting circuit 75 designates a measurement field, which is used for measuring the X-ray dose passed through the object. Based on the designated measurement field, a measurement area is set up in the imaging surface 36. The measurement area setting circuit 75 has a specified area mode and an automatic area setting mode. In the specified area mode, the measurement area setting circuit 75 sets a first measurement area in a position predetermined in accordance with the body part to be imaged. In the automatic area setting mode, the measurement area setting circuit 75 sets up a second measurement area based on the distribution of the X-ray dose measured by the plurality of measuring pixels 65.

The measurement area setting circuit 75 is switchable between the automatic area setting mode and the specified area mode in response to an input from the console 17. The console 17 is provided with an input device 105 (see FIG. 8) functioning as a mode switch. The radiological technician puts the measurement area setting circuit 75 into a desired mode by operation of the input device 105. Mode setting information inputted from the input device 105 is transmitted from the console 17 to the electronic cassette 16, and is inputted to the measurement area setting circuit 75 through the controller 41.

In the specified area mode, information of the first measurement area, which is determined in accordance with the body part designated by the console 17, is inputted to the measurement area setting circuit 75. Taking chest imaging as an example, the measurement area setting circuit 75 designates portions corresponding to right and left lung fields as first measurement areas 80 and 81, as shown by dashed lines in FIG. 4.

Figure 6:
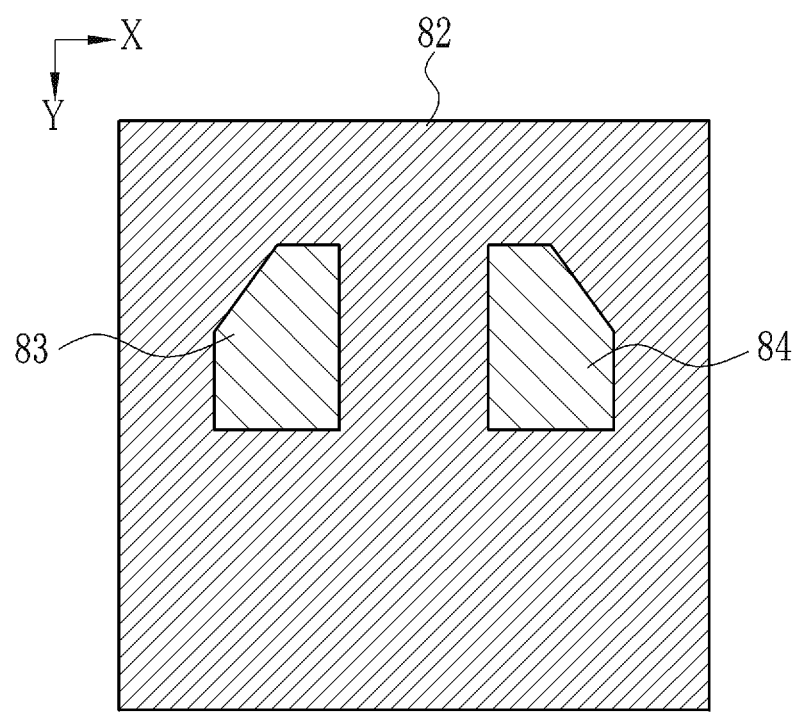
FIG. 6 is an explanatory view of second measurement fields.

In the automatic area setting mode, the measurement area setting circuit 75 analyzes the AEC measurement signals of all the measuring pixels 65 disposed in the imaging surface 36 to set up the second measurement area. FIG. 6 shows an X-ray image 82 obtained in the chest imaging, by way of example. The X-ray transmittance is higher in the portions of the right and left lung fields than in their surroundings. The measurement area setting circuit 75 compares the AEC measurement signals of the measuring pixels 65, and determines one or more areas in which the AEC measurement signal has a higher value than their surroundings. The determined areas are designated as second measurement areas 83 and 84.

The measurement area setting circuit 75 outputs the AEC measurement signals of the measuring pixels 65 disposed within the first or second measurement areas to the integration circuit 76. The integration circuit 76 calculates an average of the AEC measurement signals outputted from the measurement area setting circuit 75, and integrates the average. Upon detecting the start of the X-ray emission, the comparison circuit 77 starts monitoring an integrated value calculated by the integration circuit 76. The comparison circuit 77 compares the integrated value with an emission stop threshold value provided by the threshold value generation circuit 78 repeatedly at appropriate timing. When the integrated value has reached the emission stop threshold value, the comparison circuit 77 outputs the emission stop signal. The emission stop threshold value is set depending on the body part so as to have an appropriate X-ray dose.

In addition to above, the AEC section 67 is provided with an emission stop determination circuit that determines the stop timing of the X-ray emission by comparing the AEC measurement signals from the measuring pixels 65 with a predetermined maximum threshold value. This prevents excessive X-ray exposure of the patient even in case of failure of the comparison circuit 77.

The communication unit 40 is connected to an emission signal I/F 79, in addition to the antenna 37 and the socket 39 described above. To the emission signal I/F 79, the emission signal I/F 25 of the source controller 14 is connected. The emission signal I/F 79 performs reception of the query signal, a transmission of the emission permission signal in response to the query signal, a reception of the emission start signal, and an output of the comparison circuit 77 e.g. a transmission of the emission stop signal.

The console 17 is communicatably connected to the electronic cassette 16 in a wired or wireless method, to control the operation of the electronic cassette 16. To be more specific, the console 17 transmits the imaging condition to the electronic cassette 16 to set up a signal processing condition (e.g. gain of an amplifier for multiplying voltage corresponding to the accumulated signal charge) of the FPD 35. Additionally, the console 17 controls the operation of the electronic cassette 16, more specifically, powers on and off the electronic cassette 16, and performs mode switching into a power saving mode, an imaging preparation mode, and the like.

The console 17 applies various types of image processes such as offset correction, gain correction, and defect correction to the X-ray image data transmitted from the electronic cassette 16. In the defect correction, pixel values of the row having the measuring pixel 65 are interpolated using the pixel values of the adjacent row without having the measuring pixel 65. The X-ray image after being subjected to the image process is displayed on a monitor 104 (see FIG. 8) of the console 17. The X-ray image data is written to a storage device 102 and a memory 101 (see FIG. 8) of the console 17, or an image storage server connected to the console 17 through a network.

The console 17 receives an input of an examination order, which includes information about the sex and age of the patient, the body part to be imaged, and an imaging method, and displays the examination order on the monitor 104. The examination order is inputted from an external system e.g. HIS (hospital information system) or RIS (radiography information system) that manages patient data and examination data related to radiography, or inputted manually by the radiological technician. The examination order includes the body part to be imaged e.g. head, chest, abdomen, full spine, lower limbs, or the like, and an imaging direction e.g. anterior, medial, diagonal, PA (X-rays are applied from a posterior direction), or AP (X-rays are applied from an anterior direction). The radiological technician confirms the contents of the examination order on the monitor 104, and inputs the imaging condition corresponding to the contents through an operation screen displayed on the monitor 104.

The imaging condition set in the console 17 is different from one body part to another. As shown in FIG. 7, for example, the imaging condition includes the tube voltage, information of the first measurement area to be used in the specified area mode, the emission stop threshold value used for comparison with the integrated value of the AEC measurement signals to judge the stop of the X-ray emission, and the like. This information about the imaging conditions is stored in the storage device 102.

The information of the first measurement area is represented by X and Y coordinates. When the first measurement area is in a rectangular shape, as in the case of the above first measurement area 80, 81, for example, the X and Y coordinates of two corner points connected by a diagonal line are stored. The X and Y coordinates correspond to the position of the pixels 45 and measuring pixels 65 in the imaging surface 36 of the electronic cassette 16. An X axis extends in a direction parallel to the scan lines 51, and a Y axis extends in a direction parallel to the signal lines 52. The coordinates of the pixel 45 at the upper left corner are assigned as an origin point (0, 0).

Figure 8:
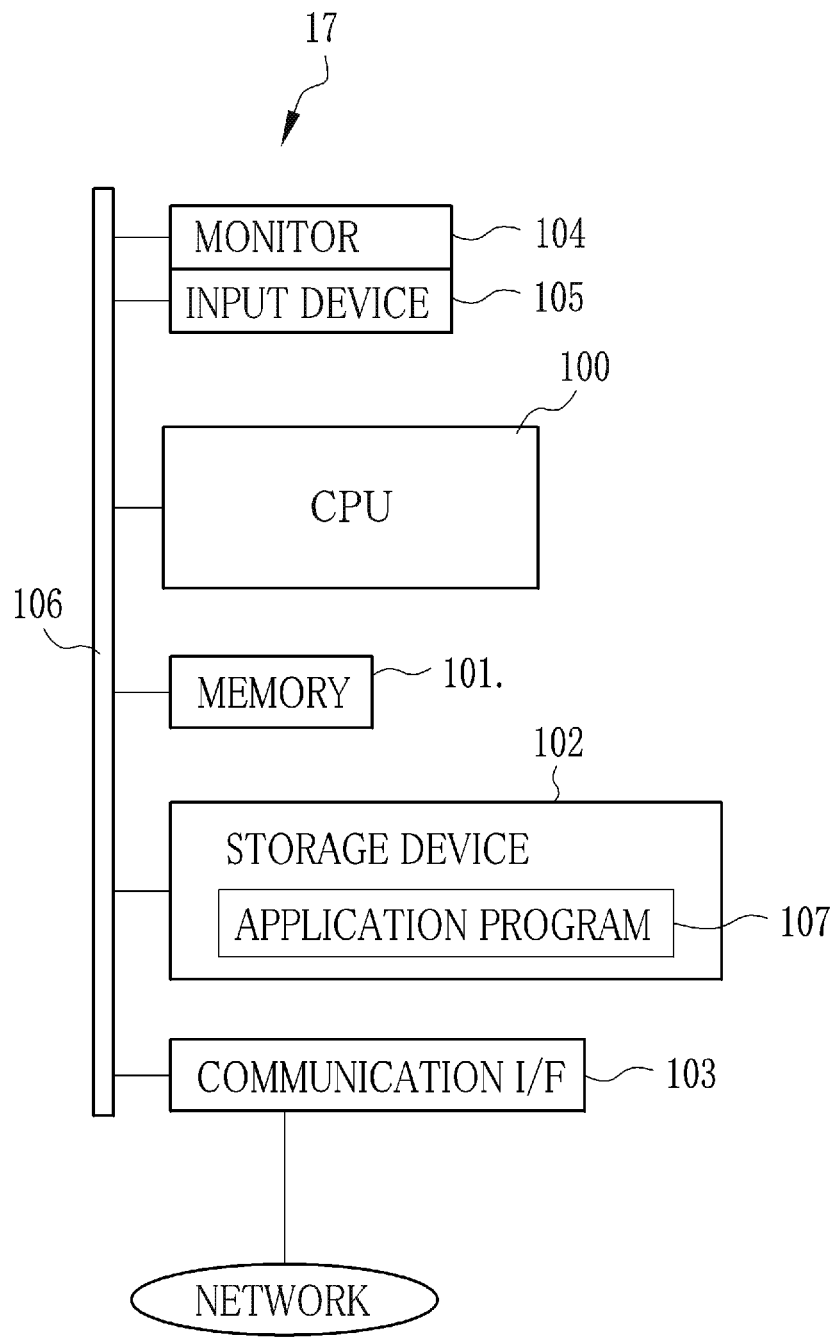
FIG. 8 is a block diagram of the console.

As shown in FIG. 8, the console 17 is composed of a computer having a CPU 100, the memory 101, the storage device 102, a communication I/F 103, the monitor 104, and the input device 105. These components are connected to each other via a data bus 106.

The storage device 102 is a hard disk drive (HDD), for example. The storage device 102 stores control programs and application programs 107. Running the application programs 107 makes the console 17 perform various functions related to the X-ray imaging, such as a display process of the examination order and the X-ray image, the image process of the X-ray image, and a setup of the imaging condition.

The memory 101 is a work memory used when the CPU 100 executes. The CPU 100 loads the control programs stored on the storage device 102 into the memory 101, and runs the programs for centralized control of the computer. The communication I/F 103 functions as a network interface for performing wireless or wired transmission control from/to an external device such as the RIS, the HIS, the image server, and the electronic cassette 16. The input device 105 includes a keyboard and a mouse, or a touch panel integrated with the monitor 104. The input device 105 is operated in a setup of the imaging condition and an input of the mode setting information.

Figure 9:
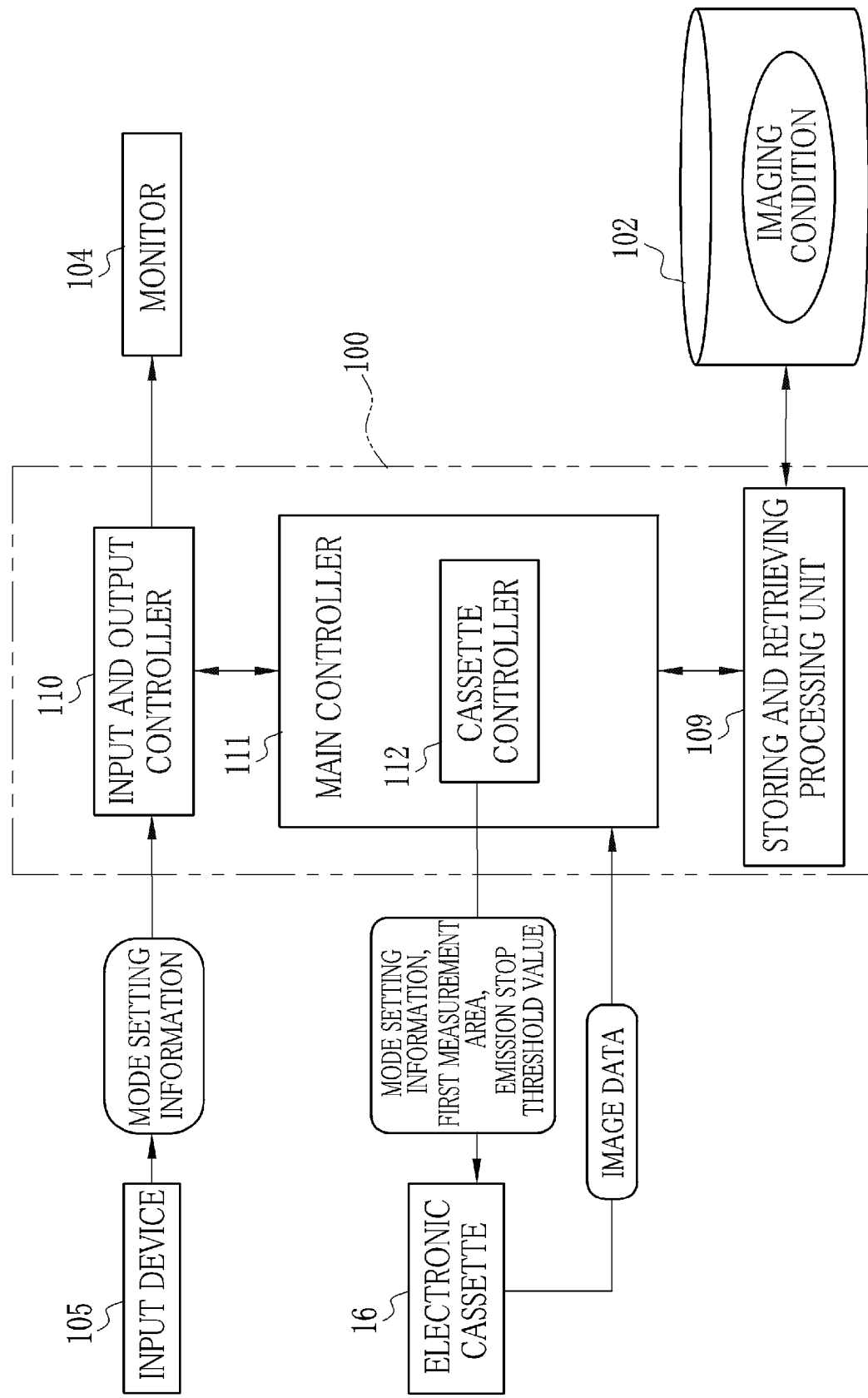
FIG. 9 is a block diagram showing the function and the information flow of the console.

As shown in FIG. 9, by running the application programs 107, the CPU 100 of the console 17 functions as a storing and retrieving processing unit 109, an input and output controller 110, and a main controller 111. The storing and retrieving processing unit 109 stores various types of data to the storage device 102, and retrieves the data from the storage device 102. The input and output controller 110 reads out drawing data from the storage device 102 in accordance with the operation of the input device 105, and outputs to the monitor 104 various types of operation screens of GUIs based on the read drawing data. The input and output controller 110 receives an input of an operation command from the input device 105 through the operation screen.

The main controller 111 performs centralized control of the console 17. Also, the main controller 111 has a cassette controller 112 that controls the operation of the electronic cassette 16. In addition to above, an image processor for applying the various types of image processes such as the offset correction, the gain correction, and the defect correction to the image data inputted from the electronic cassette 16, a communicator for mediating communication with the source controller 14 and the electronic cassette 16, and the like are established in the CPU 100. The function of each component may be embodied by hardware instead of software.

The cassette controller 112 receives the mode setting information inputted from the input device 105. The cassette controller 112 also receives the information of the first measurement area corresponding to the body part and the information of the emission stop threshold value, from the storing and retrieving processing unit 109. The cassette controller 112 provides the received information to the electronic cassette 16. Note that, when the mode setting information indicates the specified area mode, the cassette controller 112 necessarily transmits the information of the first measurement area to the electronic cassette 16. When the mode setting information indicates the automatic area setting mode, the cassette controller 112 may not transmit the information of the first measurement area to the electronic cassette 16.

Figure 10:
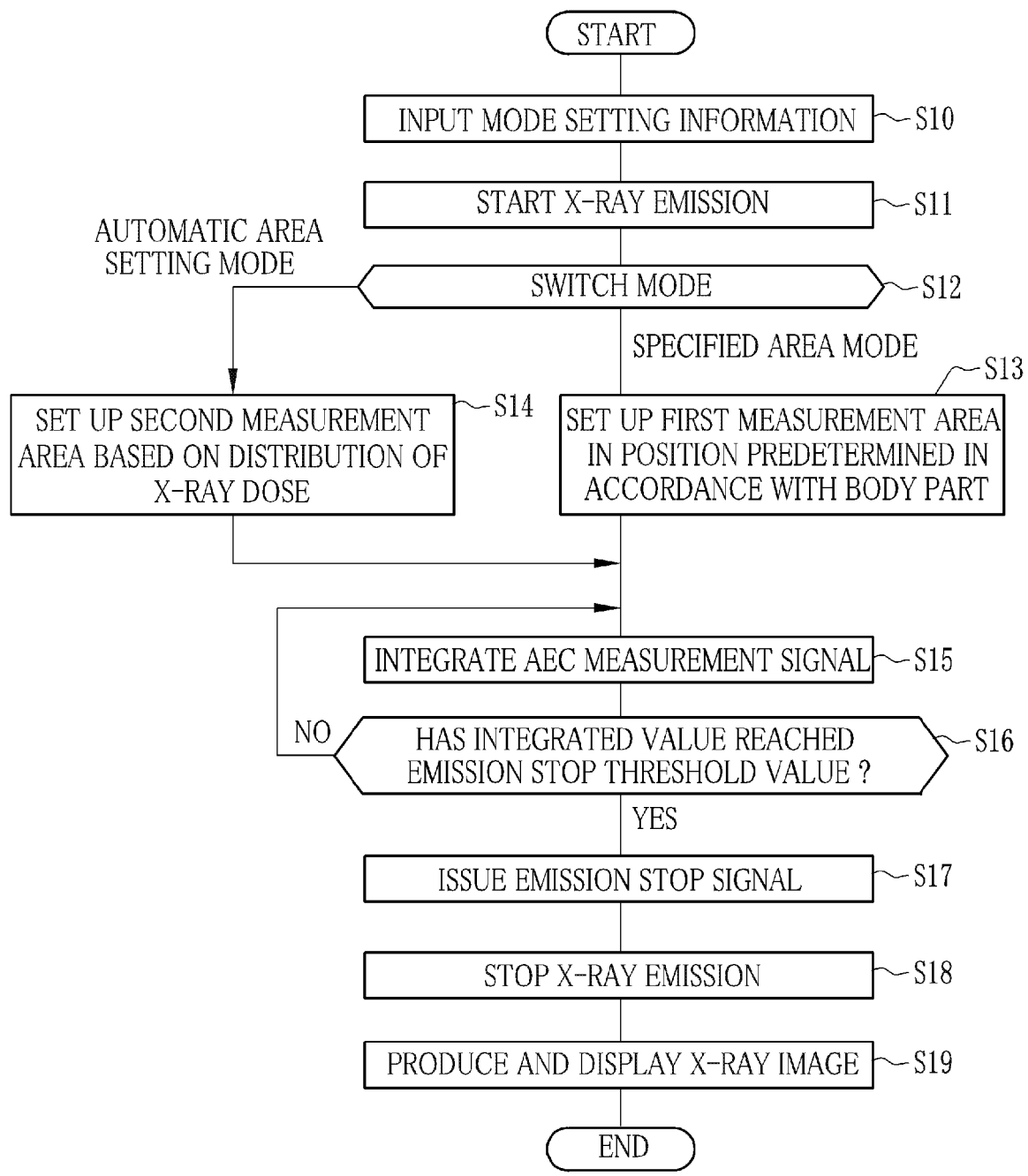
FIG. 10 is a flowchart of the operation of a first embodiment.

Next, the operation of the X-ray imaging system 10 will be described with referring to a flowchart of FIG. 10.

Firstly, while the patient M stands in a predetermined position in front of the imaging stand 30, the height and the horizontal position of the electronic cassette 16 loaded in the imaging stand 30 are adjusted to align the electronic cassette 16 with the patient's body part to be imaged. In accordance with the position of the electronic cassette 16 and the size of the body part, the height and horizontal position of the X-ray source 13 and the size of the irradiation field are adjusted. Then, the electronic cassette 16 is turned on. The radiological technician enters the imaging condition and the mode setting information from the input device 105 to the console 17 (S10). Thus, the cassette controller 112 of the console 17 sets to the electronic cassette 16 the imaging condition, the mode setting information, and the information of the measurement field, the emission stop threshold value, and the like corresponding to the imaging condition. The imaging condition is also set to the source controller 14.

After completion of imaging preparation, the emission switch 15 is half pressed. Thereby, the warm-up start signal is transmitted to the source controller 14, so the X-ray source 13 starts warming up. After a lapse of predetermined time, the emission switch 15 is fully pressed, and the emission start signal is transmitted to the source controller 14. Thus, the X-ray emission is started (S11).

Before the start of the X-ray emission, the FPD 35 of the electronic cassette 16 repeats the reset operation. Upon receiving the emission start signal from the source controller 14, the FPD 35 shifts from the reset operation to the charge accumulation operation.

At the same time as the start of the charge accumulation operation of the FPD 35, the AEC section 67 starts the AEC. The measurement area setting circuit 75 is put into the specified area mode or the automatic area setting mode, depending on the mode setting information provided by the cassette controller 112 (S12). In the specified area mode, the measurement area setting circuit 75 sets the first measurement area in a position predetermined in accordance with the body part to be imaged, based on the information of the first measurement area provided by the cassette controller 112 (S13). In the case of the chest imaging, for example, the first measurement areas 80 and 81 are set as shown in FIG. 4.

In the automatic area setting mode, the measurement area setting circuit 75 automatically sets up the second measurement area by analyzing the AEC measurement signals of the measuring pixels 65 disposed in the entire imaging surface 36 (S14), instead of using the information of the first measurement area. In the case of the chest imaging, for example, the AEC measurement signals of the measuring pixels 65 are compared with each other, and the portions in which the AEC measurement signal has a higher value than in their surroundings are determined. These areas are designated as the second measurement areas 83 and 84.

The measurement area setting circuit 75 takes out one or more AEC measurement signals outputted from the measuring pixels 65 present within the first or second measurement area, out of the AEC measurement signals of the plurality of measuring pixels 65 from the A/D 62. The taken-out AEC measurement signals are outputted to the integration circuit 76. The integration circuit 76 calculates an average of the AEC measurement signals inputted from the measurement area setting circuit 75, and integrates the average to obtain an average X-ray dose (S15).

The threshold value generation circuit 78 generates the emission stop threshold value provided by the cassette controller 112, and outputs the emission stop threshold value to the comparison circuit 77. The comparison circuit 77 compares the integrated value of the AEC measurement signals with the emission stop threshold value. When the integrated value has reached the emission stop threshold value (YES in S16), the emission stop signal is outputted. The emission stop signal is transmitted to the emission signal I/F 25 of the source controller 14 through the emission signal I/F 79 (S17).

Upon receiving the emission stop signal by the source controller 14, the controller 21 stops the electric power supply from the high voltage generator 20 to the X-ray source 13, and therefore the X-ray emission is stopped (S18). When an emission stop detection circuit of the AEC section 67 detects the stop of the X-ray emission, the FPD 35 stops the charge accumulation operation and shifts to the readout operation to output the image data. After the readout operation, the FPD 35 restarts the reset operation.

The image data outputted from the FPD 35 is transmitted to the console 17 through the communication unit 40. The image data is subjected to the various types of image processes in the console 17. The input and output controller 110 displays on the monitor 104 the processed image data as the X-ray image (S19).

According to the above embodiment, the measurement area setting circuit 75 has the specified area mode in which the measurement area is set in a position predetermined in accordance with the body part and the automatic area setting mode in which the measurement area is set up based on the distribution of the X-ray dose detected by the measuring pixels 65, and is arbitrarily switchable between the specified area mode and the automatic area setting mode. Therefore, it is possible to use one of the modes suitable for an imaging situation including a patient's condition and the body part.

The use of the automatic area setting mode eliminates the need for performing positioning between the patient's body part and the measurement field, and allows setting of the measurement field in an appropriate position based on the distribution of the X-ray dose. The automatic area setting mode is effectively used in oblique imaging in which the positional relation among the X-ray source, the body part, and the measurement field is hard to grasp. Also, the use of the automatic area setting mode prevents the AEC from being performed based on the X-ray dose that has not passed through the patient's body or the body part to be imaged. Accordingly, the AEC is appropriately carried out.

On the other hand, the X-ray emission time is more shortened in the specified area mode than in the automatic area setting mode, because the specified area mode needs less time for setting the measurement field. This reduces the X-ray exposure of the patient, and prevents the occurrence of a blur in the X-ray image due to a body motion. Also, since the positional relation between the body part and the measurement field is clear, if there is any problem in the image quality of the X-ray image or the like, the problem could be solved easily only by checking the positioning between the measurement field and the body part to be imaged.

In the above embodiment, the mode setting information is inputted from the input device 105 of the console 17, but may be inputted from the touch panel 24 of the source controller 14. The electronic cassette 16 may be provided with an operation panel specific to the input of the mode setting information.

Second to ninth embodiments will be hereinafter described. In each embodiment, the same reference numerals as those of the first embodiment indicate the same components as those of the first embodiment, and detailed description thereof will be omitted.

Second Embodiment

Figure 11:
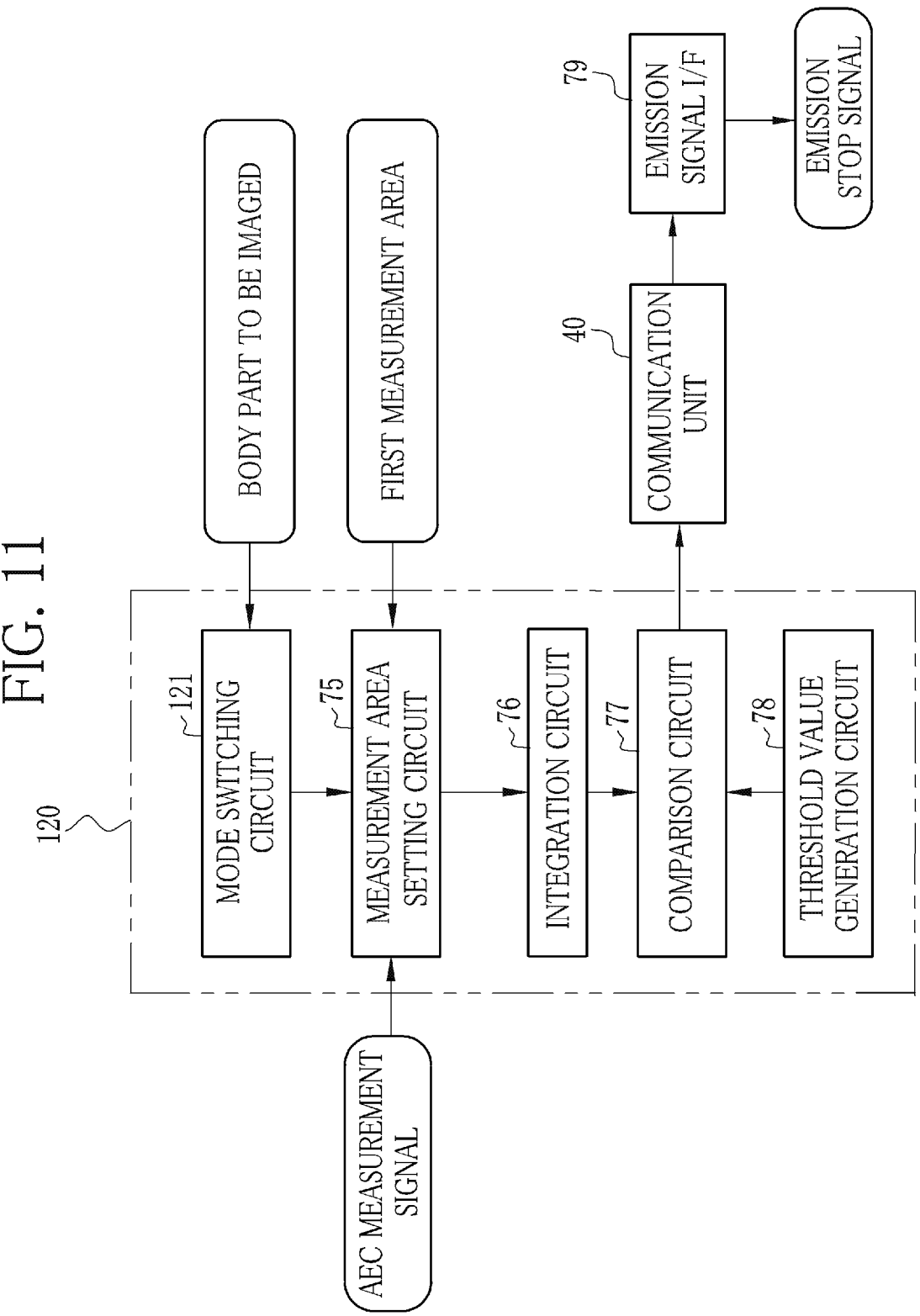
FIG. 11 is a block diagram of an AEC section of a second embodiment.

In a second embodiment, the measurement area setting circuit 75 is switched between the specified area mode and the automatic area setting mode automatically in accordance with a body part to be imaged. An AEC section 120 shown in FIG. 11 is used instead of the AEC section 67 of the first embodiment. The AEC section 120 is provided with a mode switching circuit 121.

As shown in FIG. 12, the mode switching circuit 121 has a memory that stores combinations between a body part to be imaged and a mode to be selected. For example, a body part that requires relatively short X-ray emission time, such as chest, is combined with the specified area mode, because the automatic area setting mode takes long time to set up the measurement area. A body part that requires relatively long X-ray emission time, such as lumber vertebrae, is combined with the automatic area setting mode. The oblique imaging of the chest, which requires the difficult positioning between the body part and the measurement field though its X-ray emission time is short, is combined with the automatic area setting mode. When the information of a body part to be imaged is inputted from the cassette controller 112, the mode switching circuit 121 retrieves a mode combined with the body part from the memory, and puts the measurement area setting circuit 75 into the specified mode.

Figure 13:
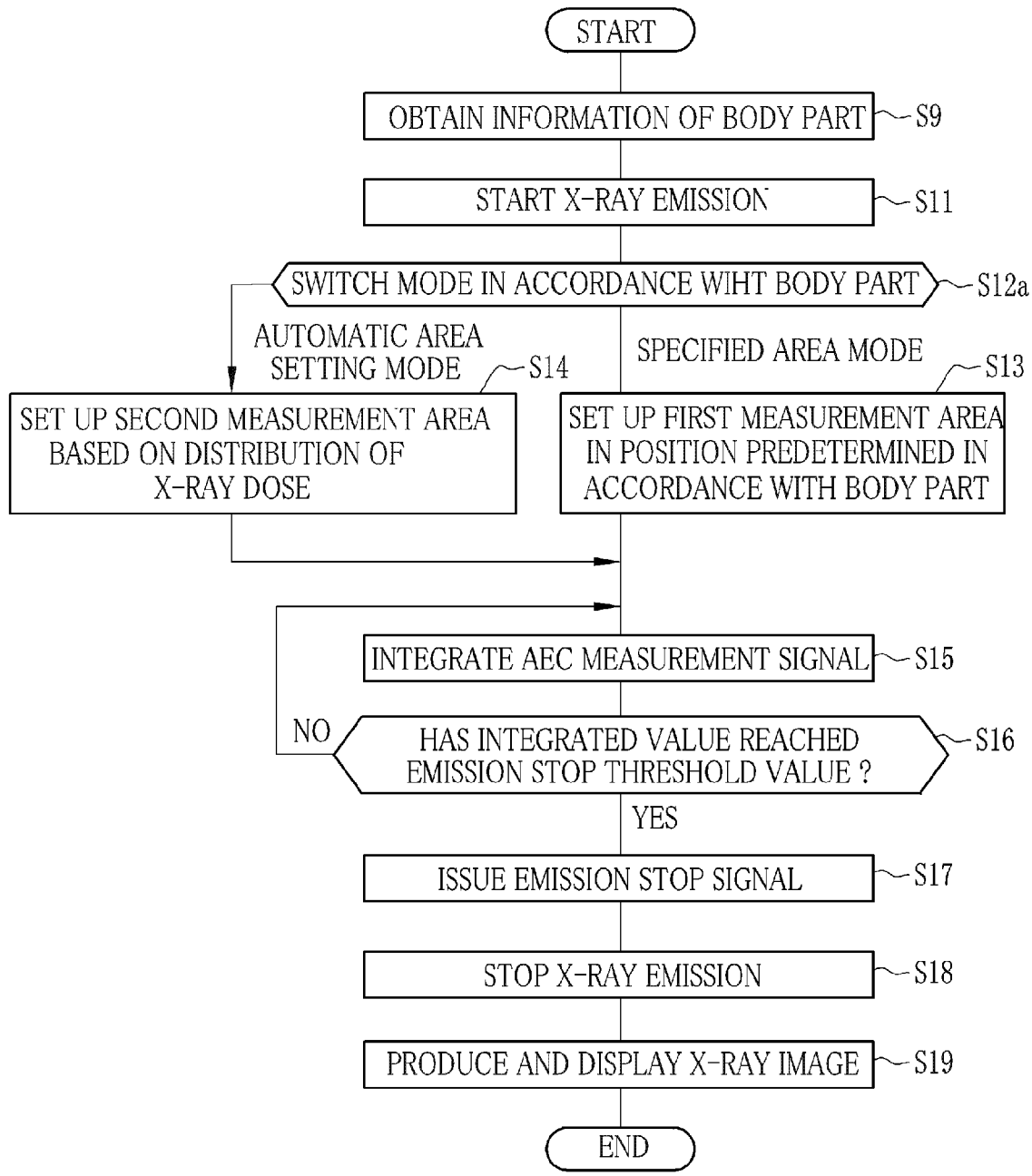
FIG. 13 is a flowchart of the operation of the second embodiment

Next, the operation of the second embodiment will be described with referring to a flowchart of FIG. 13. In this embodiment, in contrast to the first embodiment, the mode setting information is not inputted manually. Before the X-ray emission, the mode switching circuit 121 of the AEC section 120 obtains information of a body part to be imaged from the cassette controller 112 (S9), and retrieves a mode combined with the body part from the memory. For example, when the body part is chest, the specified area mode is chosen. In the case of oblique imaging of the chest, the automatic area setting mode is chosen. After that, upon starting the X-ray emission (S11), the mode switching circuit 121 puts the measurement area setting circuit 75 into the chosen mode (S12*a*).

After the switching of the mode, the measurement area setting circuit 75 sets up the first or second measurement area in accordance with the chosen mode (S13 and S14), just as with the first embodiment. Steps (S15 to S19) after that are the same as those of the first embodiment.

According to the second embodiment, the mode of the measurement area setting circuit 75 is automatically switched based on the information of the body part included in the imaging condition, without the need for inputting the mode setting information by the radiological technician. Thus, the radiological technician neither forgets about setting the mode nor mistakes a suitable mode for the other mode. In the first embodiment, there may be cases where a low-skilled technician is not sure which mode to choose and takes long time for preparation. However, this embodiment eliminates the need for choosing the mode and hence allows quick preparation.

In the second embodiment, the mode of the measurement area setting circuit 75 is switched based on the information of the body part inputted from the cassette controller 112, but may be switched based on information indicating the body part and the imaging direction instead of the information of the body part itself. This type of information includes an imaging menu, information about the imaging stand (which one of the imaging stand, an imaging table, and no stand or table is used), an imaging technique, the imaging direction (anterior, medial, diagonal, or the like), the distance (SID: source image distance) between the X-ray source 13 and the electronic cassette 16, the direction of the X-ray source 13, and the like. The use of such information allows an automatic choice of the appropriate mode, even if the information of the body part cannot be obtained.

Third Embodiment

Figure 14:
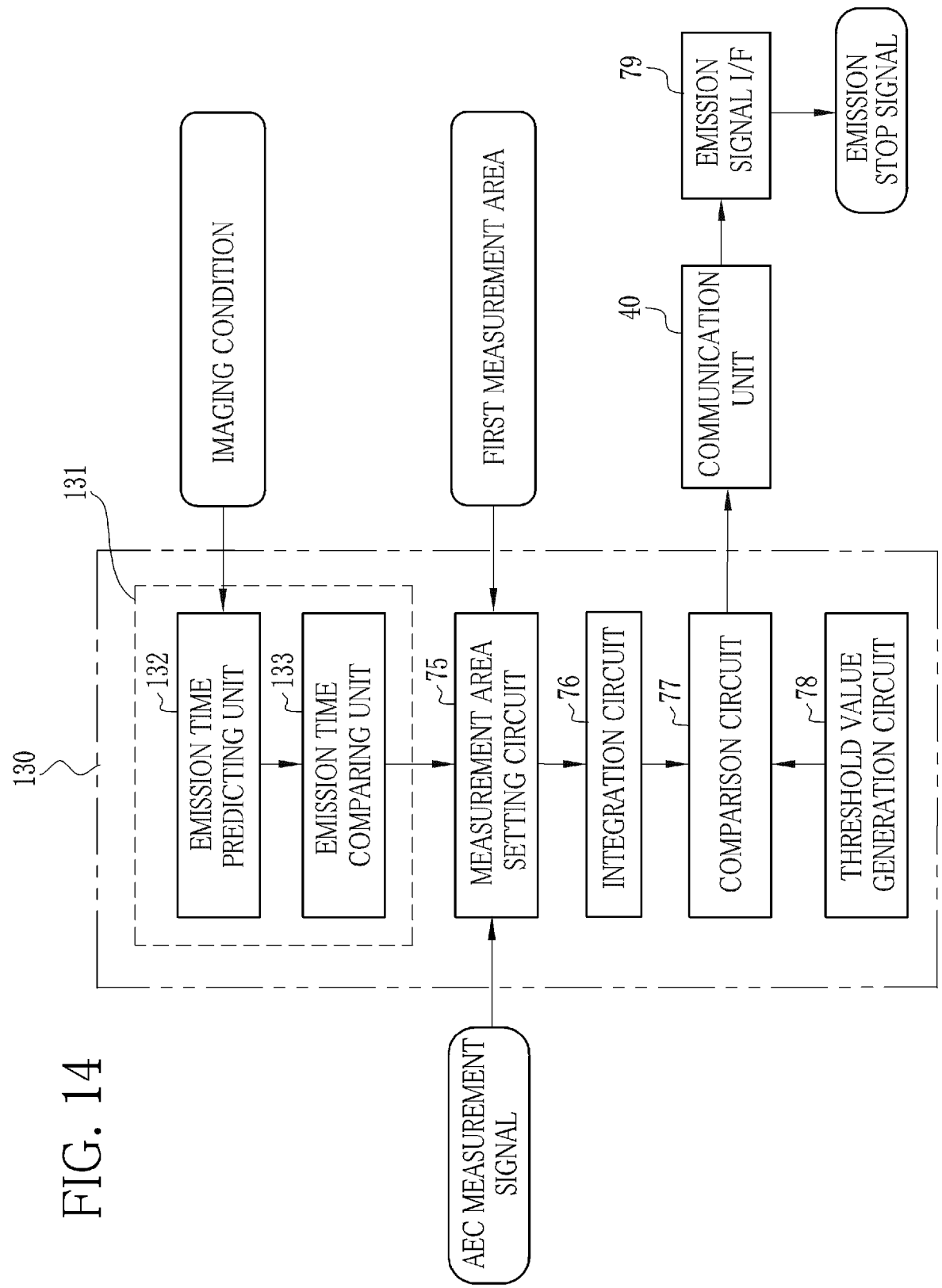
FIG. 14 is a block diagram of an AEC section according to a third embodiment.

In a third embodiment, the X-ray emission time is predicted, and the mode of the measuring area setting circuit 75 is automatically switched in accordance with the predicted emission time. An AEC section 130 shown in FIG. 14 is used instead of the AEC section 67 of the first embodiment. The AEC section 130 is provided with a mode switching circuit 131.

The mode switching circuit 131 is constituted of an emission time predicting unit 132 and an emission time comparing unit 133. The emission time predicting unit 132 predicts the X-ray emission time based on the information of the imaging condition inputted from the cassette controller 112. The imaging condition includes the body part to be imaged, the imaging menu, the information about the imaging stand, the imaging technique, the imaging direction, the SID, the direction of the X-ray source 13, and the like. For example, when the body part is chest, the predicted emission time is relatively short. When the body part is the lumber vertebrae, the predicted emission time is relatively long. The emission time comparing unit 133 compares the predicted emission time with a predetermined mode switching threshold value, and switches the mode of the measurement area setting circuit 75 according to a comparison result. The mode switching threshold value may be determined with respect to average emission time in the chest imaging, or may be set at average time required for setting the second measurement area in the automatic area setting mode.

Figure 15:
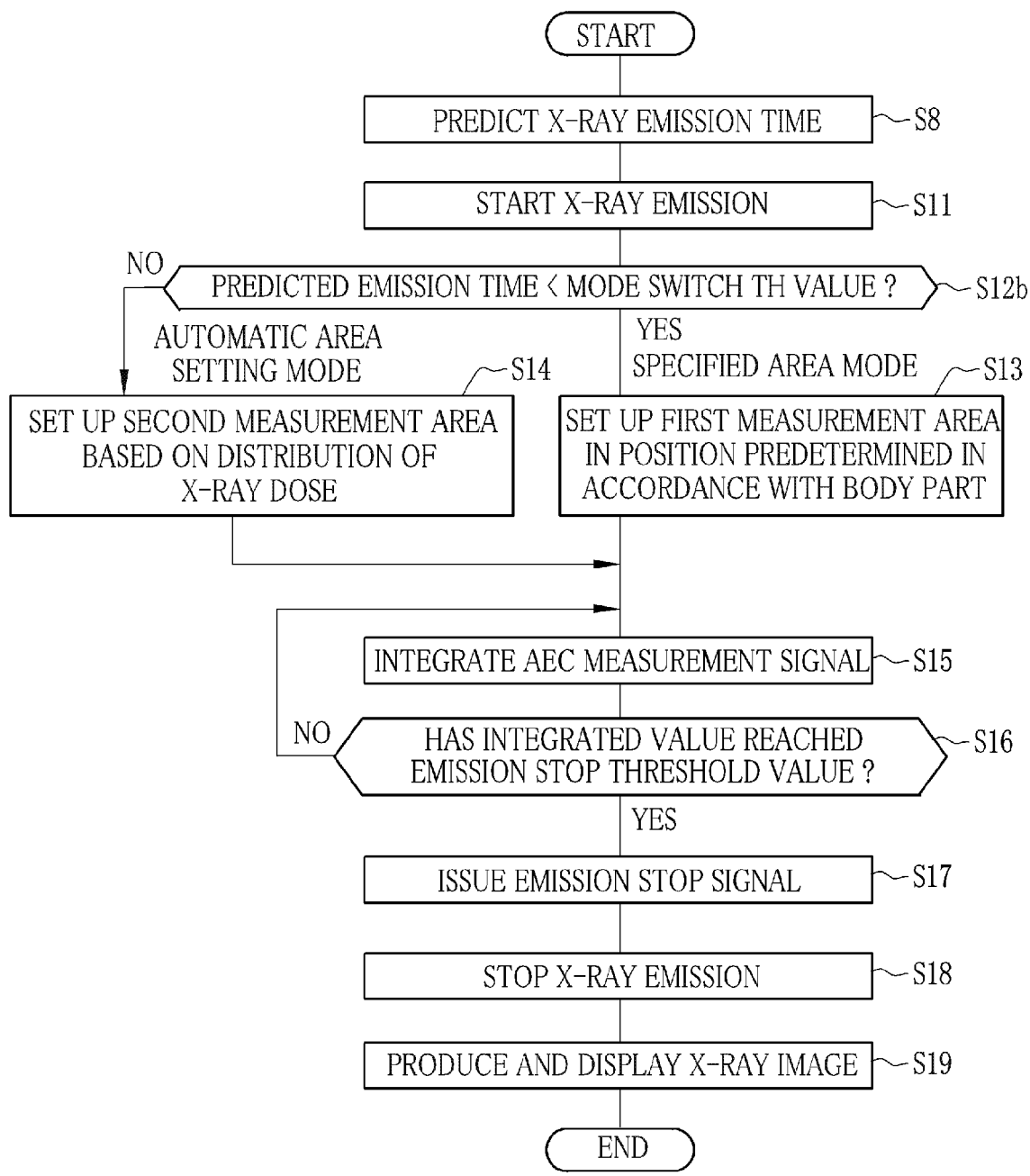
FIG. 15 is a flowchart of the operation of the third embodiment.

The operation of the third embodiment will be described with referring to a flowchart of FIG. 15. In this embodiment, as in the case of the second embodiment, the mode setting information is not manually inputted. The emission time predicting unit 132 of the mode switching circuit 131 predicts the X-ray emission time based on the imaging condition inputted from the cassette controller 112 (S8). The emission time comparing unit 133 compares the predicted emission time with the mode switching threshold value. After the start of the X-ray emission (S11), when the predicted emission time is less than the mode switching threshold value (YES in S12a), the measurement area setting circuit 75 is put into the specified area mode. When the predicted emission time is more than the mode switching threshold value (NO in S12a), the measurement area setting circuit 75 is put into the automatic area setting mode.

After the determination of the mode, the measurement area setting circuit 75 sets up the first or second measurement area in accordance with the chosen mode (S13, S14), as in the case of the first embodiment. After that, steps S15 to S19 are performed, just as with the first embodiment.

The third embodiment prevents the radiological technician from forgetting or mistaking the mode setting. Also, this embodiment saves the radiological technician from having to choose the mode and allows quick preparation, as with the second embodiment.

Fourth Embodiment

Figure 16:
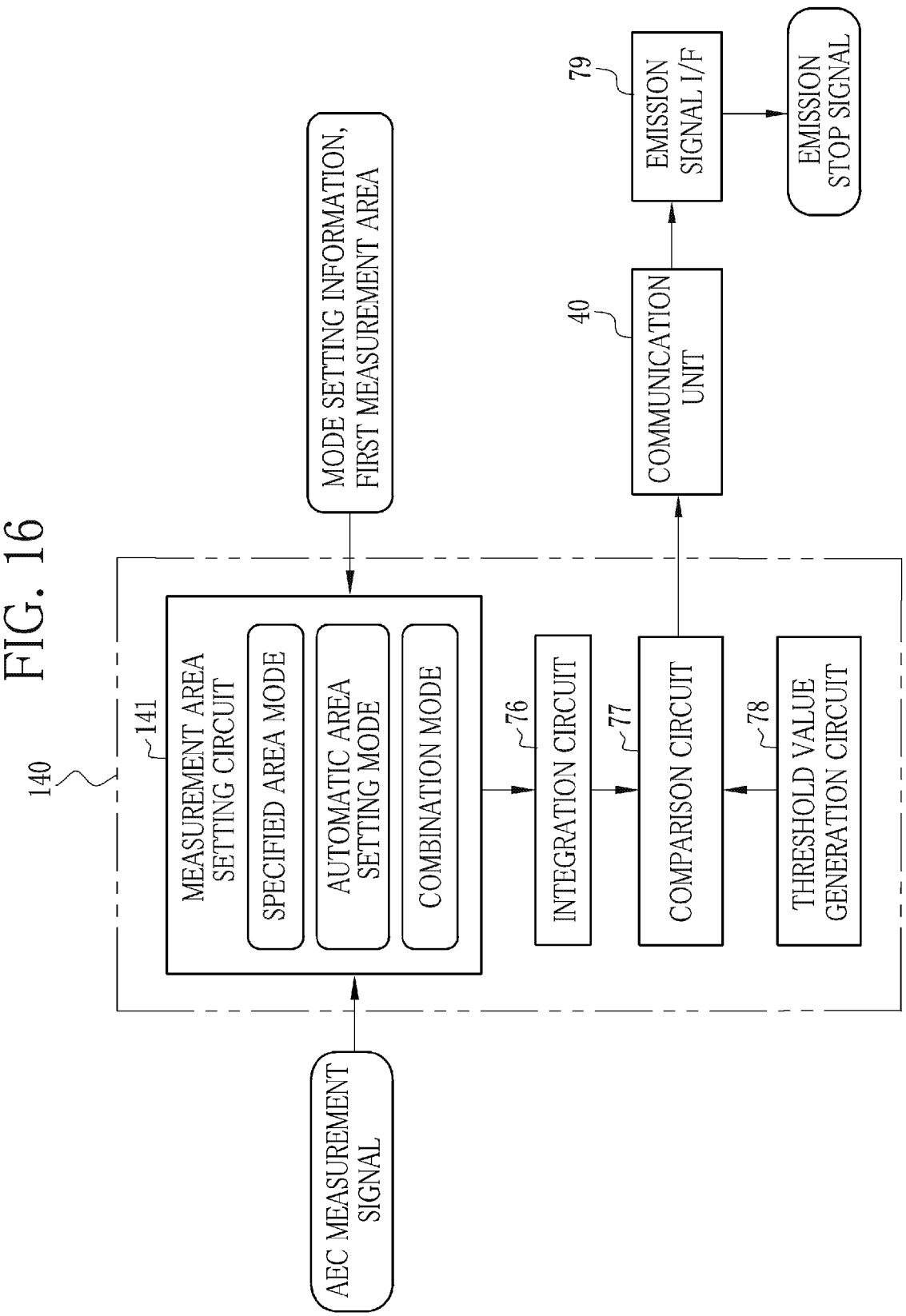
FIG. 16 is a block diagram of an AEC section according to a fourth embodiment.

In a fourth embodiment, the specified area mode and the automatic area setting mode are used in conjunction with each other. An AEC section 140 shown in FIG. 16 is used instead of the AEC section 67 of the first embodiment. The AEC section 140 is provided with a measurement area setting circuit 141 that has not only the specified area mode and the automatic area setting mode, but also a combination mode using the specified area mode and the automatic area setting mode in conjunction with each other. The measurement area setting circuit 141 is switched among the specified area mode, the automatic area setting mode, and the combination mode by the operation of the input device 105 of the console 17, as in the case of the first embodiment.

Figure 17:
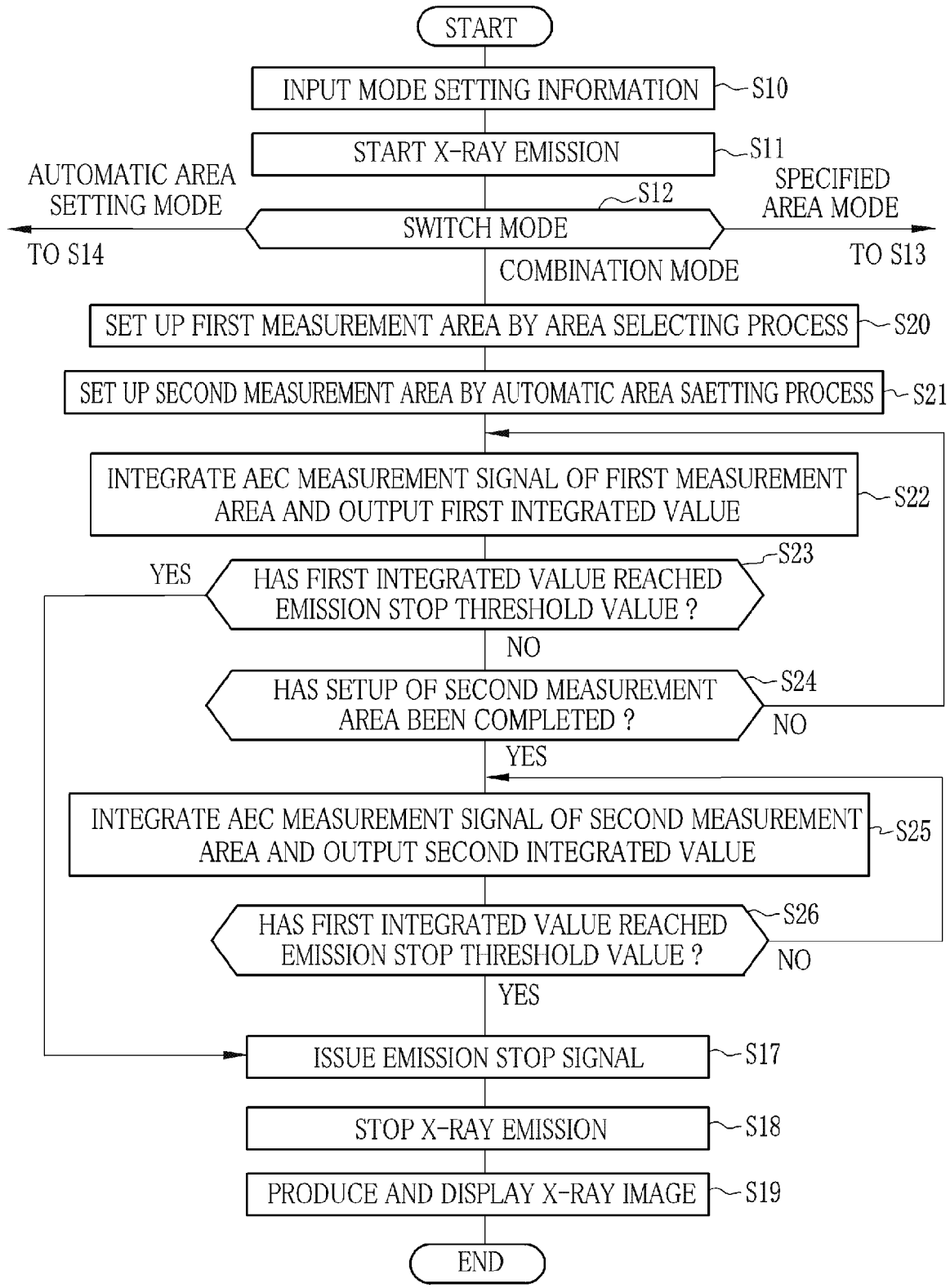
FIG. 17 is a flowchart of the operation of the fourth embodiment.

A flowchart of FIG. 17 shows operation in which the combination mode is chosen in the step of mode switching (S12). The operation of the specified area mode (S13) and the automatic area setting mode (S14) is omitted in FIG. 17. In the combination mode, the measurement area setting circuit 141 performs the same process (an area selecting process) as that of the specified area mode, in order to set the first measurement area based on the information inputted from the cassette controller 112 (S20). In parallel with the area selecting process, the measurement area setting circuit 141 performs the same process (an automatic area setting process) as that of the automatic area setting mode, in order to start setting the second measurement area based on the AEC measurement signals of the measuring pixels 65 (S21). The measurement area setting circuit 141 outputs the AEC measurement signals of the measuring pixels 65 present within the first measurement area to the integration circuit 76. The integration circuit 76 integrates the average of the AEC measurement signals, and outputs a first integrated value (S22).

The comparison circuit 77 compares the first integrated value with the emission stop threshold value (S23). When the first integrated value has reached the emission stop threshold value (YES in S23), the comparison circuit 77 outputs the emission stop signal (S17). In response to the emission stop signal, the X-ray emission is stopped (S18). Then, the X-ray image is produced and displayed (S19).

On the other hand, when the first integrated value has not reached the emission stop threshold value (NO in S23), it is checked whether or not the setup of the second measurement area has been completed (S24). When the setup of the second measurement area has been completed (YES in S24), the integration circuit 76 stops calculating the first integrated value. The integration circuit 76 integrates the average of the AEC detection signals of the measuring pixels 65 present within the second measurement area, and outputs a second integrated value (S25). The comparison circuit 77 compares the second integrated value with the emission stop threshold value (S26). By stopping the X-ray emission based on the second integrated value, the X-ray imaging is completed (S17 and S18). In other words, if the setup of the second measurement area has been completed (YES in S24) before the X-ray emission is stopped based on the first integrated value (NO in S23), the AEC is performed based on the second measurement area.

When the setup of the second measurement area has not been completed (NO in S24), an operation flow returns to S22, so the output of the first measurement value (S22) and the comparison between the first integrated value and the emission stop threshold value (S23) are performed again. In other words, if the X-ray emission is stopped based on the first integrated value prior to the setup of the second measurement area (YES in S23), the AEC is performed based on the first measurement area.

According to the fourth embodiment, one of the first and second measurement areas is used in accordance with the actual imaging situation, so the AEC is performed optimally.

Fifth Embodiment

Figure 18:
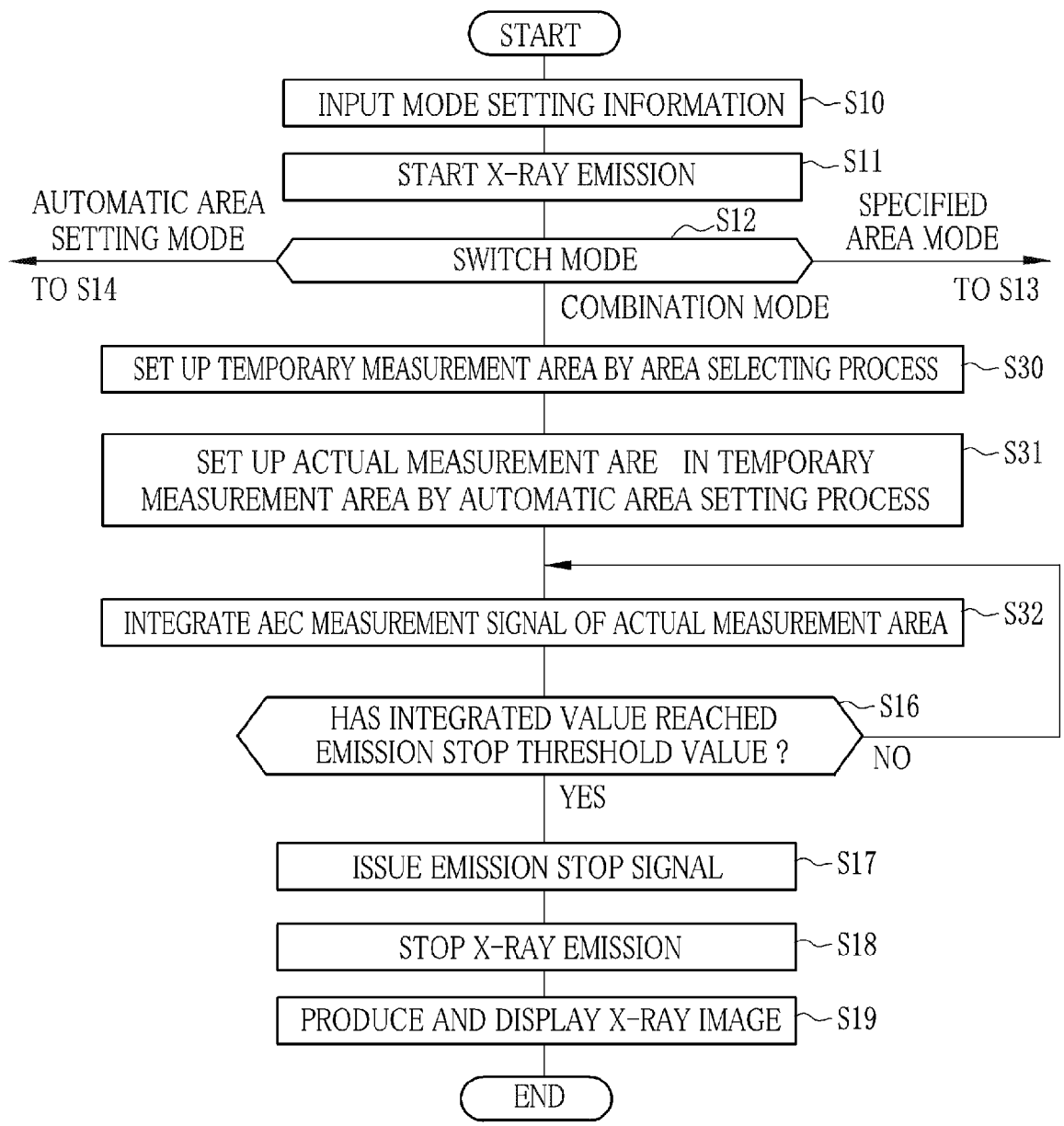
FIG. 18 is a flowchart of the operation of a fifth embodiment.
Figure 19:
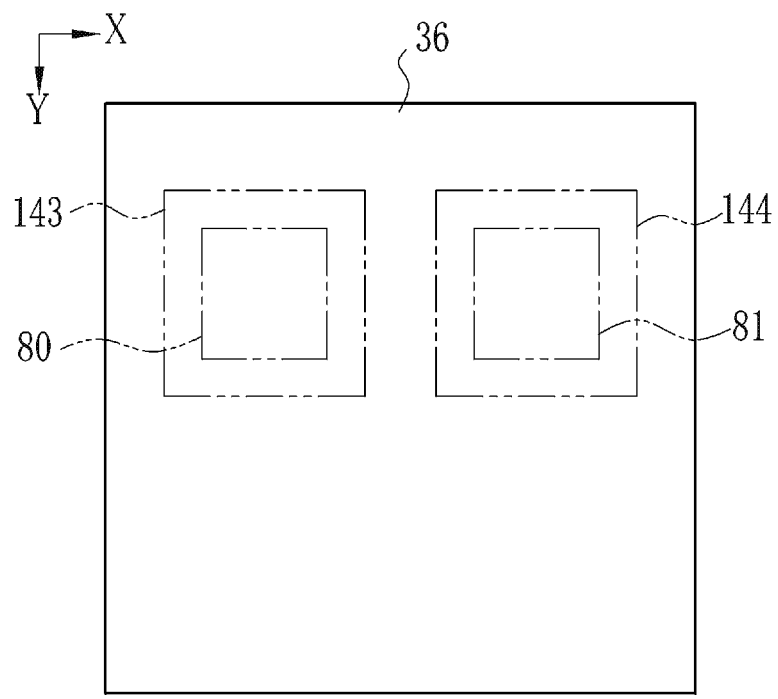
FIG. 19 is an explanatory view of temporary measurement fields.
Figure 20:
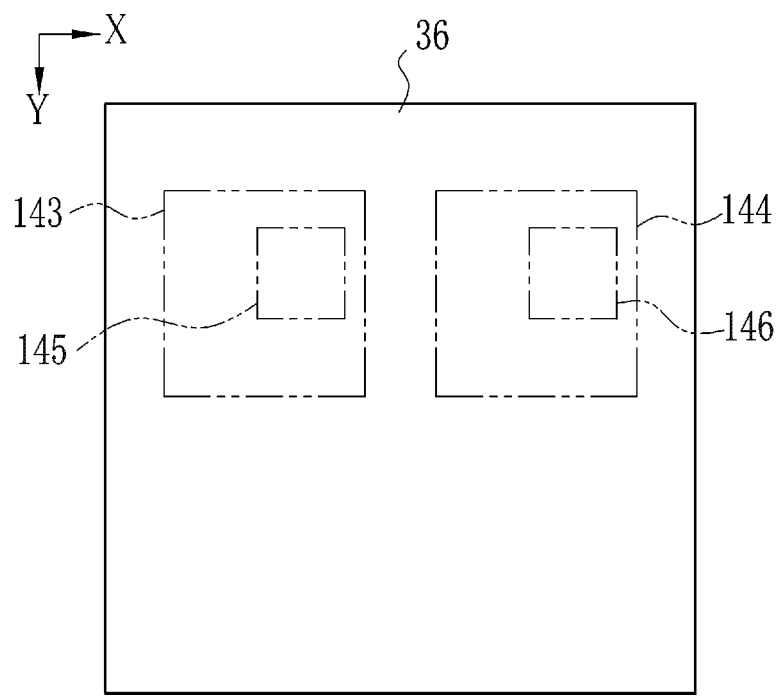
FIG. 20 is an explanatory view of actual measurement fields set up within the temporary measurement fields.

A fifth embodiment has the combination mode, as with the fourth embodiment. The fifth embodiment uses the AEC section 140 of FIG. 16, which is used in the fourth embodiment too. A flowchart of FIG. 18 shows the operation in which the combination mode is chosen in the step of mode switching (S12). The measurement area setting circuit 141 performs the area selecting process by which a temporary measurement area is set up based on information inputted from the cassette controller 112 (S30). Taking chest imaging as an example, temporary measurement areas 143 and 144 are set up in positions corresponding to the right and left lung fields, as shown in FIG. 19. Note that, the temporary measurement area 143, 144 set up in the combination mode is larger in size than the first measurement area 80, 81 set up in the specified area mode.

Then, the measurement area setting circuit 141 performs the automatic area setting process, and sets up actual measurement areas 145 and 146 in the temporary measurement areas 143 and 144, respectively (S31). The measurement area setting circuit 141 outputs to the integration circuit 76 the AEC measurement signals of the measuring pixels 65 present within the actual measurement areas 145 and 146. The integration circuit 76 integrates the average of the AEC measurement signals (S32). After that, as with the first embodiment, steps from S16 to S19 are performed and the X-ray imaging is completed.

According to the fifth embodiment, the actual measurement area is set up by the automatic area setting process in the temporary measurement area, which is smaller in size than the imaging surface 36 of the FPD 35. Thus, it is possible to set up the measurement area in a short time, as compared with the case of setting up the measurement area in the entire imaging surface 36. Therefore, it is possible to adopt the automatic area setting mode in imaging having the short X-ray emission time, such as the chest imaging. Also, since the temporary measurement area set in the combination mode is larger in size than the first measurement area set in the specified area mode, the setting accuracy of the actual measurement area is improved.

Sixth Embodiment

Figure 21:
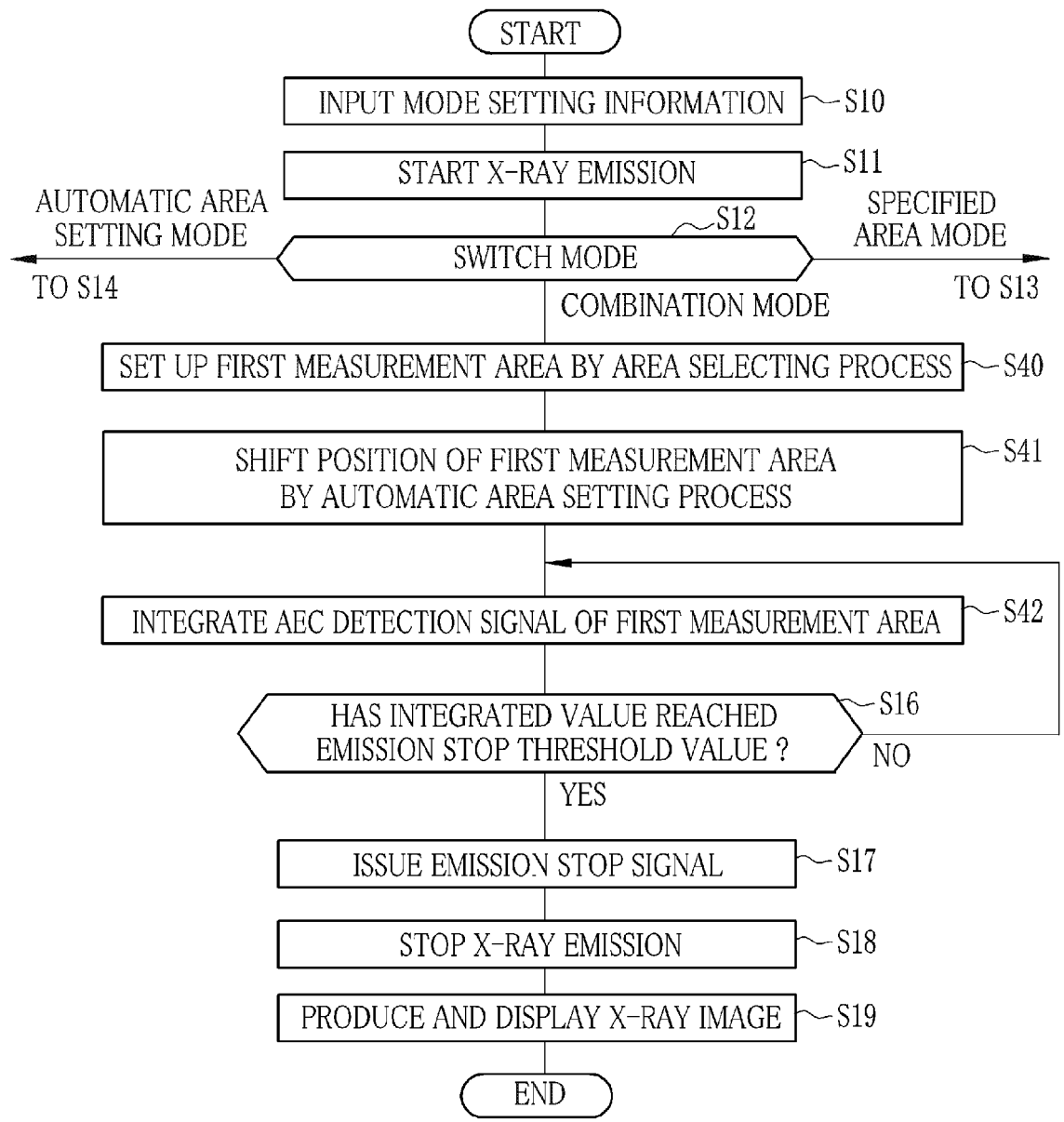
FIG. 21 is a flowchart of the operation of a sixth embodiment.
Figure 22:
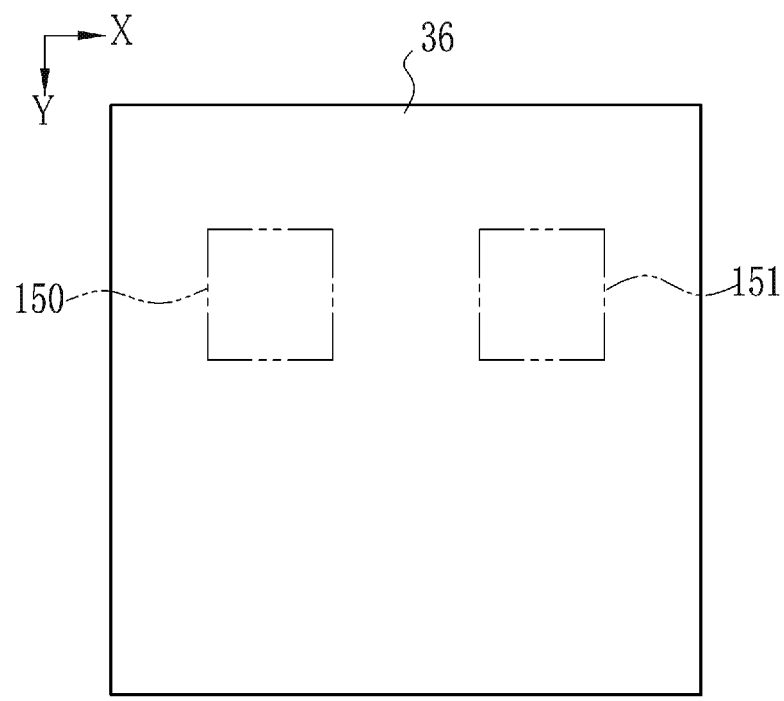
FIG. 22 is an explanatory view of first measurement fields set in the sixth embodiment.
Figure 23:
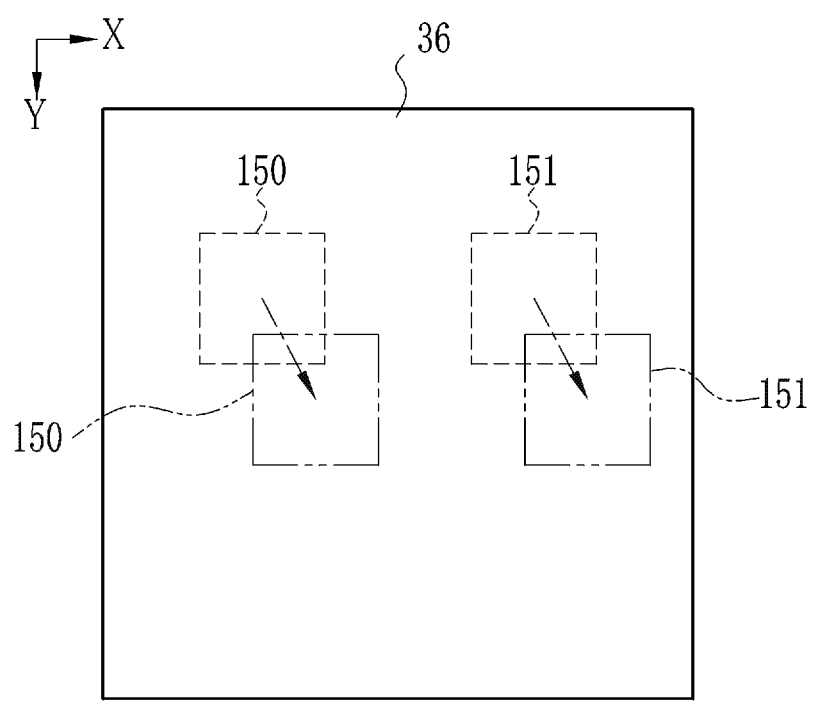
FIG. 23 is an explanatory view for explaining a shift of the position of the first measurement fields set in the sixth embodiment.

A sixth embodiment has the combination mode, as with the fourth and fifth embodiments. The sixth embodiment uses the AEC section 140 of FIG. 16, which is used in the fourth embodiment too. A flowchart of FIG. 21 shows the operation in which the combination mode is chosen in the step of mode switching (S12). In the combination mode, the measurement area setting circuit 141 performs the area selecting process in order to set up the first measurement area based on the information from the cassette controller 112 (S40). Taking chest imaging as an example, first measurement areas 150 and 151 are set up in positions corresponding to the right and left lung fields, as shown in FIG. 22.

The measurement area setting circuit 141 performs the automatic area setting process in the entire imaging surface 36, in parallel with the area selecting process. Based on the distribution of the X-ray dose obtained by the automatic area setting process, the positions of the first measurement areas 150 and 151 are shifted (S41). At this time, the shape, size, and number of the first measurement areas 150 and 151 are not changed. The measurement area setting circuit 141 outputs to the integration circuit 76 the AEC measurement signals of the measuring pixels 65 present within the first measurement areas 150 and 151. The integration circuit 76 integrates the average of the AEC measurement signals (S42). After that, as with the first embodiment, steps from S16 to S19 are performed and the X-ray imaging is completed.

According to the sixth embodiment, only the positions of the first measurement areas are adjusted without changing the shape, size, and number of the first measurement areas. Thus, it is possible to shorten process time, as compared with the case of setting up a new measurement area in the automatic area setting mode. Therefore, it is possible to adopt this embodiment in imaging having the short X-ray emission time such as the chest imaging, and have the same effect as the automatic area setting mode does.

Seventh Embodiment

Figure 24:
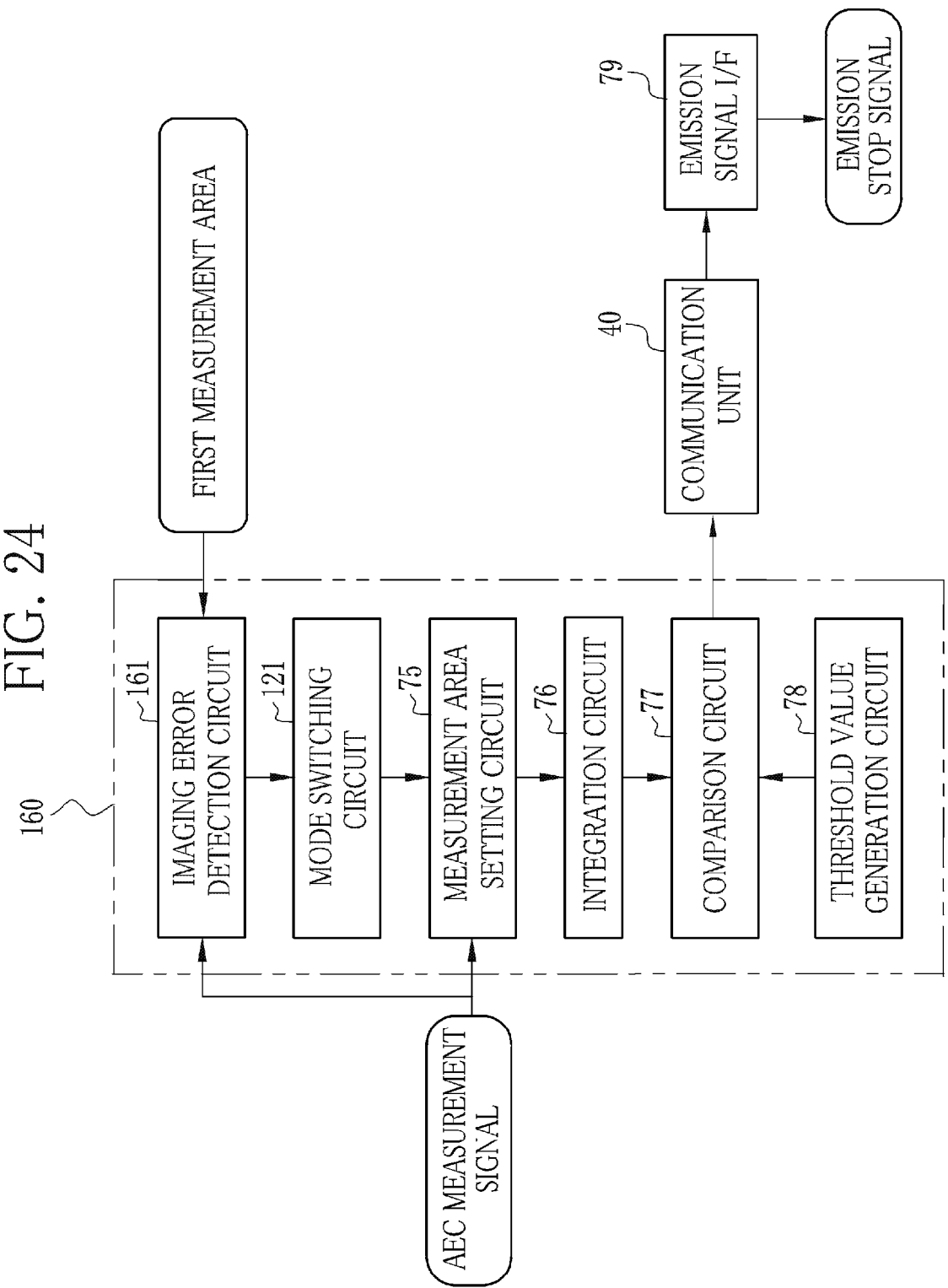
FIG. 24 is a block diagram of an AEC section according to a seventh embodiment.

An AEC section 160 shown in FIG. 24 is used instead of the AEC section 67 of the first embodiment. The AEC section 160 is provided with an imaging error detection circuit 161 for detecting an imaging error based on signal values of the AEC measurement signals of the measuring pixels 65 present within the first measurement area. For example, when the signal value of the AEC measurement signal is too high or low, the imaging error detection circuit 161 judges there is an imaging error. If the signal value of the AEC measurement signal is too high, it is estimated that the X-rays are directly incident on the first measurement area. If the signal value of the AEC measurement signal is too low, it is estimated that the first measurement area deviates from the irradiation field of the X-rays. Thus, by the detection of the imaging error, it is judged whether or not the positioning between the first measurement field (the first measurement area) and the body part is appropriate.

When the imaging error is detected, the imaging error detection circuit 160 transmits a signal that commands switching to the automatic area setting mode to the mode switching circuit 121. In response to this signal, the mode switching circuit 121 puts the measurement area setting circuit 75 into the automatic area setting mode. When the imaging error is not detected, the imaging error detection circuit 160 transmits a signal that commands switching to the specified area mode to the mode switching circuit 121. In response to this signal, the mode switching circuit 121 puts the measurement area setting circuit 75 into the specified area mode.

Figure 25:
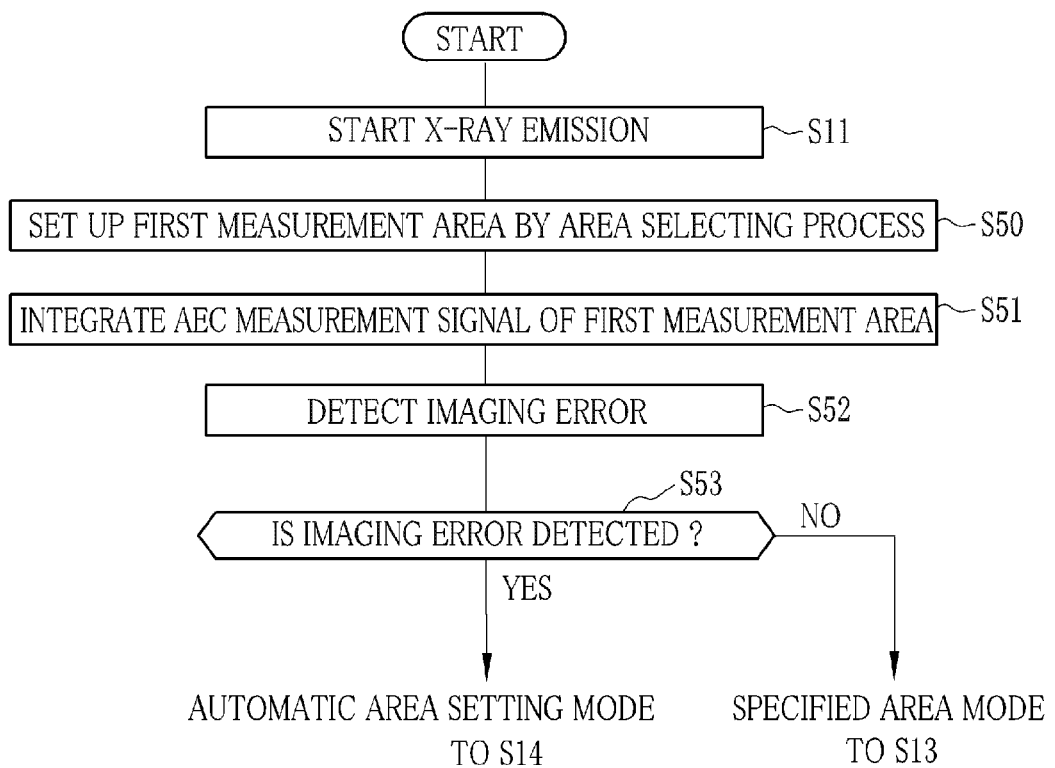
FIG. 25 is a flowchart of the operation of the seventh embodiment.

In a flowchart of FIG. 25, the measurement area setting circuit 75 performs the area selecting process by which the first measurement area is set based on the information of the first measurement area inputted from the cassette controller 112 (S50). The measurement area setting circuit 75 outputs the AEC measurement signals of the measuring pixels 65 present within the first measurement area to the integration circuit 76. The integration circuit 76 integrates the average of the AEC measurement signals, and outputs the integrated value (S51).

The imaging error detection circuit 161 detects the imaging error based on the integrated value (S52). When the imaging error is detected (YES in S53), the signal that commands switching to the automatic area setting mode is transmitted, so the AEC is performed in the automatic area setting mode (S14 to S19). On the other hand, when the imaging error is not detected (NO in S53), the signal that commands switching to the specified area mode is transmitted, so the AEC is performed in the specified area mode (S13 to S19). Note that, in the specified area mode, it is not necessary to re-perform the step of setting the first measurement area, and the first measurement area set in S50 is usable as is.

According to the seventh embodiment, when the imaging error occurs in the specified area mode, the measurement area setting circuit 75 is automatically switched to the automatic area setting mode. This allows reduction in the occurrence of the imaging error and re-imaging.

In the seventh embodiment, the imaging error is detected after the imaging is actually started. However, the possibility of the occurrence of the imaging error may be judged based on the body part to be imaged and the position, size, and shape of the first measurement area. A warning may be issued when the possibility is high.

Eighth Embodiment

In the above embodiments, since the normal pixels 45 and the measuring pixels 65 functioning as the dose measuring sensors are independent from each other, it is necessary to perform the defect correction by which the pixel value corresponding to the position of the measuring pixel 65 is interpolated with the pixel value of the normal pixel 45 adjoining to the measuring pixel 65. The defect correction may cause deterioration in the image quality of the X-ray image. Accordingly, the use of an FPD 170 having structure as shown in FIG. 26 eliminates the need for the defect correction.

Figure 26:
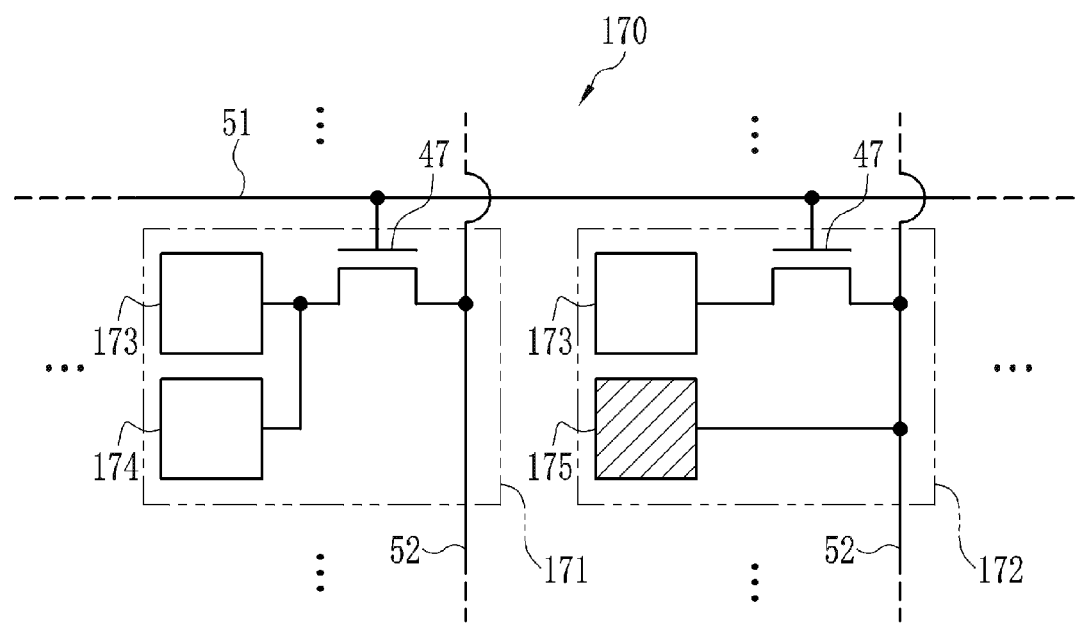
FIG. 26 is an explanatory view of an FPD according to an eighth embodiment.

In FIG. 26, the FPD 170 includes first pixels 171 for specific use in image detection and second pixels 172 for use in the image detection and the AEC. The first and second pixels 171 and 172 are arranged into a matrix at an appropriate ratio, as with the normal pixels 45 and the measuring pixels 65 of the above embodiment. Each first pixel 171 has two photodiodes 173 and 174. Each second pixel 172 has two photodiodes 173 and 175. The photodiodes 173 and 174 of the first pixel 171 are connected in parallel, and one end is connected to the signal line 52 through the TFT 47. In the second pixel 172, on the other hand, an end of the photodiode 173 is connected to the signal line 52 through the TFT 47, but the photodiode 175 is directly connected to the signal line 52 without through the TFT 47. In other words, the photodiode 175 of the second pixel 172 has the same structure as the measuring pixel 65 of the above embodiments.

From the first pixel 171, electric charge accumulated in the two photodiodes 173 and 174 is read out. From the second pixel 172, on the other hand, electric charge accumulated only in the photodiode 173 is read out. Since electric charge produced in the photodiode 175 is used for the AEC and does not contribute the production of the X-ray image, the second pixel 172 has a less pixel value than the first pixel 171. In a case where the same X-ray dose is applied to the photodiodes 173 to 175 of the same size, the pixel value of the second pixel 172 is approximately a half of that of the first pixel 171. However, the deterioration in the image quality of the X-ray image is prevented as compared with the above embodiments requiring the defect correction. The X-ray image can be produced without the defect correction by multiplying the output of the second pixel 172 by a coefficient, which is calculated in advance based on the size of the photodiodes 173 to 175. This almost completely eliminates an adverse effect on the X-ray image quality that is caused by providing the measuring pixels for specific use in the AEC in the FPD.

Ninth Embodiment

Figure 27:
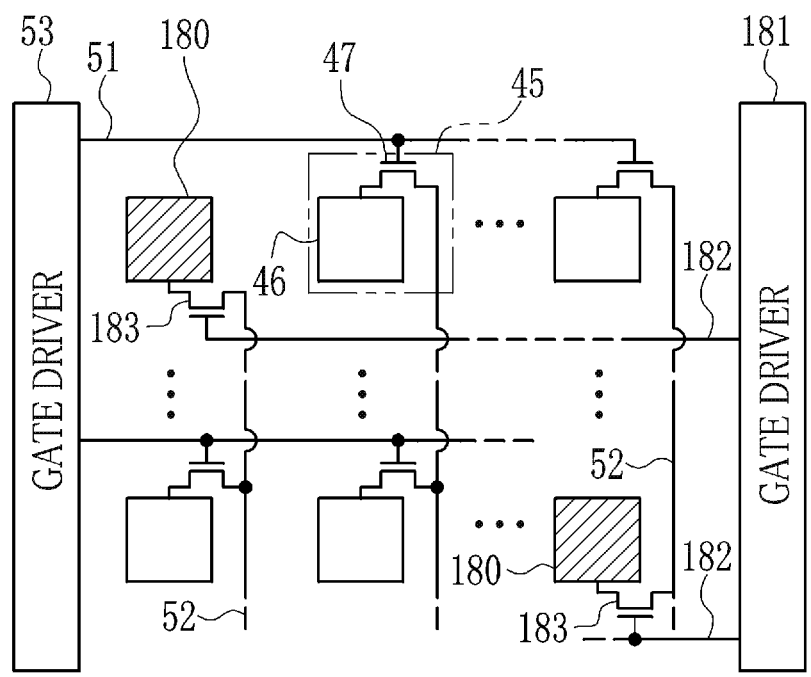
FIG. 27 is an explanatory view of an FPD according to a ninth embodiment.

In the above first to seventh embodiments, the measuring pixel 65 that is directly connected to the signal line 52 without through the TFT 47 is used as the dose measuring sensor. However, as shown in FIG. 27, a measuring pixel 180 may be connected to a TFT 183 driven by a gate driver 181 and a scan line 182 that are different from the gate driver 53 and the scan lines 51 of the normal pixels 45. Electric charge accumulated in the measuring pixel 180 can be read out independently of that in the normal pixels 45. Alternatively, with taking advantage of the fact that electric current flowing through the bias line 48 for supplying the bias voltage Vb to each normal pixel 45 is in proportion to the amount of the electric charge produced in the normal pixel 45, the electric current flowing through the bias line 48 connected to the specific pixel may be monitored to detect the X-ray dose. In another case, the X-ray dose may be measured based on leak current from the normal pixels 45 in a state where all the TFTs 47 are turned off. In further another case, another AEC measuring pixel that has different structure and an independent output may be provided coplanarly to the imaging surface 36 separately from the normal pixels 45.

The electronic cassette 16 and the imaging stand 30 are separate in the above embodiments, but an FPD-integrated imaging stand may be used instead. The console 17 and the electronic cassette 16 are separate in the above embodiments, but the console 17 may not be necessarily independent of the electronic cassette 16. The electronic cassette 16 may have the function of the console 17. Likewise, the source controller 14 and the console 17 may be integrated into one unit. The present invention may be applied to a stand-mount type X-ray image detecting device, instead of or in addition to the electronic cassette being a portable type X-ray image detecting device.

The present invention is applicable to a radiation imaging system using another type of radiation such as γ-rays instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image detecting device comprising:
   (A) a detection panel having an imaging surface having a plurality of pixels arranged in two dimensions, for detecting a radiation image of an object from electric charge accumulated in said pixels in accordance with radiation emitted from a radiation source and passed through said object;
   (B) a plurality of dose measuring sensors disposed in said imaging surface;
   (C) an AEC section for performing automatic exposure control based on signals from said dose measuring sensors, said AEC section including:
   a measurement area setting circuit for setting a measurement area to be used for measuring a radiation dose on said imaging surface, said measurement area setting circuit being switchable between a specified area mode for performing an area selecting process to set up a first measurement area in a position predetermined in accordance with a body part to be imaged and an automatic area setting mode for performing an automatic area setting process to set up a second measurement area based on distribution of said radiation dose measured by said dose measuring sensors;
   a mode switching circuit for switching said measurement area setting circuit between said specified area mode and said automatic area setting mode;
   an integration circuit for integrating said signal from said dose measuring sensor present within said first or second measurement area, in order to obtain an integrated value corresponding to said radiation dose; and a comparison circuit for comparing said integrated value with a predetermined emission stop threshold value, wherein when said integrated value has reached said emission stop threshold value, the comparison circuit outputs an emission stop signal to stop radiation emission from said radiation source.

2. The radiation image detecting device according to claim 1, wherein said mode switching circuit chooses one of said specified area mode and said automatic area setting mode in response to an operation from outside.

3. The radiation image detecting device according to claim 1, wherein said mode switching circuit chooses one of said specified area mode and said automatic area setting mode in accordance with said body part of said object.

4. The radiation image detecting device according to claim 1, wherein said mode switching circuit includes:
an emission time predicting unit for predicting emission time of said radiation based on an imaging condition;
an emission time comparing unit for comparing said predicted emission time with a predetermined mode switching threshold value; and
wherein, said mode switching circuit chooses said specified area mode when said predicted emission time is less than said mode switching threshold value, and chooses said automatic area setting mode when said predicted emission time is more than said mode switching threshold value.

5. The radiation image detecting device according to claim 1, wherein said measurement area setting circuit further has a combination mode for using said specified area mode and said automatic area setting mode in conjunction with each other, and said mode switching circuit switches said measurement area setting circuit among said specified area mode, said automatic area setting mode, and said combination mode.

6. The radiation image detecting device according to claim 5, wherein when said measurement area setting circuit is put into said combination mode, said AEC section performs the steps of:
setting up said first measurement area by said area selecting process;
starting setting up said second measurement area by said automatic area setting process, in parallel with said area selecting process;
integrating said signal from said dose measuring sensor present within said first measurement area with use of said integration circuit, to calculate a first integrated value corresponding to said radiation dose;
comparing said first integrated value with said emission stop threshold value;
when said first integrated value has reached said emission stop threshold value, outputting said emission stop signal in order to stop said radiation emission from said radiation source;
when setup of said second measurement area is completed before said first integrated value has reached said emission stop threshold value, said integration circuit stopping calculating said first integrated value, and integrating said signal from said dose measuring sensor present within said second measurement area to calculate a second integrated value; and
when said second integrated value has reached said emission stop threshold value, outputting said emission stop signal in order to stop said radiation emission from said radiation source.

7. The radiation image detecting device according to claim 5, wherein when said measurement area setting circuit is put into said combination mode, said AEC section performs the steps of:
setting up a temporary measurement area by said area selecting process;
setting up an actual measurement area in said temporary measurement area by performing said automatic area setting process in said temporary measurement area; and
performing said automatic exposure control by using said radiation dose measured by said dose measuring sensor present within said actual measurement area.

8. The radiation image detecting device according to claim 7, wherein said temporary measurement area is larger in size than said first measurement area.

9. The radiation image detecting device according to claim 5, wherein when said measurement area setting circuit is put into said combination mode, said AEC section performs the steps of:
setting up said first measurement area by said area selecting process;
performing said automatic area setting process in parallel with said area selecting process; and
adjusting a position of said first measurement area based on distribution of said radiation dose obtained by said automatic area setting process.

10. The radiation image detecting device according to claim 5, wherein said AEC section further includes:
an imaging error detection circuit for detecting an imaging error based on said radiation dose measured by said dose measuring sensor present within said first measurement area, wherein
when said imaging error detection circuit detects said imaging error, said mode switching circuit chooses said automatic area setting mode; and
when said imaging error detection circuit detects no imaging error, said mode switching circuit chooses said specified area mode.

11. The radiation image detecting device according to claim 1, wherein said plurality of pixels include:
a plurality of normal pixels each for performing accumulation of said electric charge and readout of said electric charge to a signal line in accordance with operation of a switching element; and
a plurality of measuring pixels each being connected to said signal line directly without through said switching element and used as said dose measuring sensor.

12. The radiation image detecting device according to claim 1, wherein said plurality of pixels include:
a plurality of normal pixels each for performing accumulation of said electric charge and readout of said electric charge to a signal line in accordance with operation of a first switching element; and
a plurality of measuring pixels each being connected to a second switching element and used as said dose measuring sensor.

13. A control method of a radiation image detecting device including a detection panel having an imaging surface having a plurality of pixels arranged in two dimensions and detecting a radiation image of an object from electric charge accumulated in said pixels in accordance with radiation emitted from a radiation source and passed through said object, a plurality of dose measuring sensors disposed in said imaging surface, and an AEC section for performing automatic exposure control based on signals from said dose measuring sensors, said control method comprising the steps of:

switching said AEC section between a specified area mode and an automatic area setting mode, an area selecting process being performed in said specified area mode to set up a first measurement area in a position predetermined in accordance with a body part to be imaged of said object, an automatic area setting process being performed in said automatic area setting mode to set up a second measurement area based on distribution of a radiation dose measured by said dose measuring sensors;

performing a chosen one of said area selecting process and said automatic area setting process in order to set up one of said first and second measurement areas;

integrating a signal from said dose measuring sensor present within said one of said first and second measurement areas to obtain an integrated value corresponding to said radiation dose;

comparing said integrated value with a predetermined emission stop threshold value; and when said integrated value has reached said emission stop threshold value, outputting an emission stop signal to stop radiation emission from said radiation source.

14. A radiation imaging system comprising:
(A) a radiation source for emitting radiation;
(B) a radiation image detecting device for detecting a radiation image from said radiation emitted from said radiation source and passed through an object, said radiation image detecting device including:
(b1) a detection panel having an imaging surface having a plurality of pixels arranged in two dimensions, for detecting said radiation image from electric charge accumulated in said pixels in accordance with said radiation incident on said pixels;
(b2) a plurality of dose measuring sensors disposed in said imaging surface;
(b3) an AEC section for performing automatic exposure control based on signals from said dose measuring sensors, said AEC section including:
a measurement area setting circuit for setting a measurement area to be used for measuring a radiation dose on said imaging surface, said measurement area setting circuit being switchable between a specified area mode for performing an area selecting process to set up a first measurement area in a position predetermined in accordance with a body part to be imaged and an automatic area setting mode for performing an automatic area setting process to set up a second measurement area based on distribution of said radiation dose measured by said dose measuring sensors;
a mode switching circuit for switching said measurement area setting circuit between said specified area mode and said automatic area setting mode;
an integration circuit for integrating said signal from said dose measuring sensor present within said first or second measurement area, in order to obtain an integrated value corresponding to said radiation dose; and
a comparison circuit for comparing said integrated value with a predetermined emission stop threshold value, wherein when said integrated value has reached said emission stop threshold value, the comparison circuit outputs an emission stop signal to stop radiation emission from said radiation source.

* * * * *